United States Patent
Jamieson et al.

(10) Patent No.: US 10,001,485 B2
(45) Date of Patent: Jun. 19, 2018

(54) METHODS FOR SENSITIZING A QUIESCENT CANCER STEM CELL TO A BCR-ABL INHIBITOR

(71) Applicant: The Regents of the University of California, Oakland, CA (US)

(72) Inventors: Catriona H. Jamieson, La Jolla, CA (US); Daniel Goff, La Jolla, CA (US); Kristen Smith, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 616 days.

(21) Appl. No.: 14/349,310

(22) PCT Filed: Nov. 7, 2012

(86) PCT No.: PCT/US2012/064000
§ 371 (c)(1),
(2) Date: Apr. 2, 2014

(87) PCT Pub. No.: WO2013/070807
PCT Pub. Date: May 16, 2013

(65) Prior Publication Data
US 2014/0288087 A1    Sep. 25, 2014

Related U.S. Application Data

(60) Provisional application No. 61/556,629, filed on Nov. 7, 2011.

(51) Int. Cl.
| | | |
|---|---|---|
| *G01N 33/574* | (2006.01) | |
| *C12Q 1/68* | (2018.01) | |
| *A61K 45/06* | (2006.01) | |
| *A61K 31/166* | (2006.01) | |
| *A61K 31/506* | (2006.01) | |

(52) U.S. Cl.
CPC ....... *G01N 33/5748* (2013.01); *A61K 31/166* (2013.01); *A61K 31/506* (2013.01); *A61K 45/06* (2013.01); *C12Q 1/6886* (2013.01); *G01N 33/57426* (2013.01); *C12Q 2600/106* (2013.01); *C12Q 2600/158* (2013.01); *G01N 2510/00* (2013.01); *G01N 2800/52* (2013.01)

(58) Field of Classification Search
CPC ............................ A61K 31/166; A61K 31/506
USPC ......................................................... 514/616
See application file for complete search history.

(56) References Cited

FOREIGN PATENT DOCUMENTS

| | | | |
|---|---|---|---|
| JP | 2007-159416 | * | 6/2007 |
| WO | WO2010/120943 | * | 10/2010 |
| WO | WO2011/044375 | * | 4/2011 |

OTHER PUBLICATIONS

Li (Cancer Res 2006 vol. 66 No. 9 pp. 4553-4557).*
Tauchi et al. Activity of ABT-737, an Inhibitor of BCL-2 Family Proteins, in Imatinib-or Dasatinib-Resistant CML Cells: Involvement of BCL-2 Family Proteins for Drug Resistance. Blood 106(11), p. 3364 (2005) (abstract).*
Hallaert et al. c-Abl kinase inhibitors overcome CD40-mediated drug resistance in CLL: implications for therapeutic targeting of chemoresistant niches. Blood 112(13), pp. 5141-5149 (2008).*
Wei et al. BI-97C1, an Optically Pure Apogossypol Derivative as Pan-Active Inhibitor of Antiapoptotic B-Cell Lymphoma/Leukemia-2 (Bcl-2) Family Proteins. J. Med. Chem. 53, pp. 4166-4176 (2010).*

* cited by examiner

*Primary Examiner* — Jeffrey S Lundgren
*Assistant Examiner* — Sara E Townsley
(74) *Attorney, Agent, or Firm* — Greer, Burns & Crain; Gregory P. Einhorn

(57) ABSTRACT

The disclosure provides methods for determining the self-renewal potential of a cancer stem cell (CSC), or for predicting the drugability (susceptibility to a drug) of a CSC, and/or for predicting the progression of a cancer that corresponds to the CSC. In alternative embodiments, the disclosure provides methods for determining whether a CSC in a niche is more pro-apoptotic or more anti-apoptotic in relation to a normal stem cell or a CSC from another niche. In alternative embodiments, the disclosure provides methods for determining the prognosis or malignant potential of a cancer. In alternative embodiments, the disclosure provides methods determining the anti-apoptotic versus a pro-apoptotic potential of a cancer stem cell (CSC).

7 Claims, 8 Drawing Sheets

SEQUENCE LISTING

<160> NUMBER OF SEQ ID NOS: 14

<210> SEQ ID NO 1
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 1
atgtgtgtgg agagcgtcaa                                               20

<210> SEQ ID NO 2
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 2
ttcagagaca gccaggagaa a                                             21

<210> SEQ ID NO 3
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 3
agaccttacg acgggttgg                                                19

<210> SEQ ID NO 4
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 4
aatcctgccc cagtttgtta                                               20

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
gaggaggacg agttgtaccg                                               20

<210> SEQ ID NO 6
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 6
actccacaaa cccatccttg                                               20

<210> SEQ ID NO 7
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 7
catggcagca gtaaagcaag                                            20

<210> SEQ ID NO 8
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 8
gaaggagaaa aaggccacaa                                            20

<210> SEQ ID NO 9
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 9
gctgggaaaa tggctttg                                              18

<210> SEQ ID NO 10
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 10
tcagaaaaat taggccggtt t                                          21

<210> SEQ ID NO 11
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 11
ctccagactg tccacagcat                                            20

<210> SEQ ID NO 12
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 12
ccctgaggct caaagtcaga                                            20

<210> SEQ ID NO 13
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 13
cgtcttgctc gagatgtgat g                                          21

```
<210> SEQ ID NO 14
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 14
tttatagccc cccttgagca c                                              21
```

METHODS FOR SENSITIZING A QUIESCENT CANCER STEM CELL TO A BCR-ABL INHIBITOR

CROSS REFERENCE TO RELATED APPLICATIONS

This application is a U.S. national stage filing under 35 U.S.C. § 371 of PCT patent application no. PCT/US2012/064000, filed Nov. 7, 2012, which claims the benefit of priority under 35 U.S.C. § 119(e) to U.S. Provisional Application Ser. No. 61/556,629 entitled, "METHODS FOR DETERMINING CANCER STEM CELL SUSCEPTIBILITY TO TREATMENTS AND THERAPIES," filed Nov. 7, 2011, all of which are incorporated by reference herein in their entireties, including all figures.

FIELD OF THE INVENTION

This disclosure relates to cellular biology, medicine and oncology. In alternative embodiments, the disclosure provides methods for determining the self-renewal potential of a cancer stem cell (CSC), or for predicting the drugability (susceptibility to a drug) of a CSC, and/or for predicting the progression of a cancer that corresponds to the CSC. In alternative embodiments, the disclosure provides methods for determining whether a CSC in a niche is more pro-apoptotic or more anti-apoptotic in relation to a normal stem cell or a CSC from another niche. In alternative embodiments, the disclosure provides methods for determining the prognosis or malignant potential of a cancer. In alternative embodiments, the disclosure provides methods determining the anti-apoptotic versus a pro-apoptotic potential of a cancer stem cell (CSC).

BACKGROUND OF THE DISCLOSURE

A growing body of evidence suggests that a relatively rare subset of cells within a cancer subverts properties normally ascribed to stem cells in regenerating tissues, such as enhanced self-renewal and survival capacity, which render these cancer stem cells (CSC) resistant to treatments that target rapidly dividing cells (Visvader, J. E. *Nature* 469, 314-322 (2011); Guzman, M. L., et al. *Proc Natl Acad Sci USA* 99, 16220-16225 (2002).

Chronic Myeloid Leukemia (CML) progresses from early, Chronic Phase (CP) to the more advanced Blast Crisis (BC) stage. With progression to blast crisis (BC), CML stem cells become more resistant to therapies targeting BCR-ABL. As BCR-ABL targeted therapy initiates apoptosis, these results suggest that CML CSC may become increasingly resistant to apoptosis with progression. B-cell lymphoma-2 (Bcl-2, or BCL2) family isoform expression is a critical player in the progression from CP to BC.

The BCL2 family is comprised of a diverse set of genes that integrate pro-survival and pro-death stimuli and modulate the permeability of the mitochondrial membrane (Reed, J. C. *Blood* 111, 3322-3330 (2008)). Activation of mitochondrial outer membrane permeability (MOMP) results in activation of a caspase cascade triggering apoptosis. Pro-survival BCL2 family genes contribute to leukemogenesis (Beverly, L. J. & Varmus, H. E. *Oncogene* 28, 1274-1279 (2009)), CML progression, TKI resistance (Jaiswal, S. et al. cited above; Sanchez-Garcia, I. & Grutz, G., *Proc Natl Acad Sci USA* 92, 5287-5291 (1995); Horita, M., et al. *J Exp Med* 191, 977-984 (2000); Aichberger, K. J., et al. *Blood* 105, 3303-3311 (2005); Konopleva, M., et al. *Br J Haematol* 118, 521-534 (2002) and hematopoietic stem and progenitor cell survival (Milyaysky, M., et al. *Cell Stem Cell* 7, 186-197 (2010); Domen, J. & Weissman, I. L. *Exp Hematol* 31, 631-639 (2003)) by direct inhibition of MOMP.

Existing methods for predicting leukemia progression and drug susceptibility analyze the bulk of cells from a leukemia and do not quantitate BCL2 family molecules. However, not all cells in a leukemia are equivalent and CSC in particular display aberrant expression of BCL2 molecules. Because CSC drive the progression of leukemia, analysis and characterization of that population specifically could allow for better prediction of the course of the disease.

CSC in bone and bone marrow niches are especially resistant to treatment. This may be due to increased quiescence (exit from the cell cycle) of CSC in the niche as well as increased survival related to aberrant ratios of BCL2 family isoforms.

SUMMARY OF THE INVENTION

In alternative embodiments, the disclosure herein provides methods for determining the self-renewal potential of a cancer stem cell (CSC), or for predicting the drugability (susceptibility to a drug) of a CSC, and/or for predicting the progression of a cancer that corresponds to the CSC, the method comprising:
(a) (i) providing at least one or a plurality of CSCs, or at least one or a plurality of CSCs from a niche;
(ii) detecting and quantifying in the at least one or a plurality of CSCs:
(1) one or more B-cell lymphoma-2 (BCL2) family protein(s) or protein isoform(s), and/or, a transcript (mRNA, message) encoding one or more BCL2 family protein(s) or protein isoform(s), and
(2) the cell cycle status or the amount of quiescence, or exit from the cell cycle, of the CSC; and
(iii) comparing (1) the quantified levels of protein or transcript in the CSC to a cell having a comparable normal (wild type) phenotype or a CSC from another niche, or the amount of one protein isoform to a second protein isoform (of the same protein), or the amount of transcript encoding one protein isoform to the amount of transcript encoding a second protein isoform (of the same protein), and (2) the cell cycle status or the amount of quiescence, or exit from the cell cycle, of the CSC comparable to a normal (wild type) CSC or a CSC from another niche; wherein the combination of
(1) increased amount of quiescence, or exit from the cell cycle, in the CSC as compared to a cell having a comparable normal (wild type) phenotype or a CSC from another niche, and
(2) more amount of a longer splice form of a BCL2 family protein transcript as compared to a shorter alternative splice isoform of the BCL2 family transcript, and/or more amount of a protein encoded by a longer splice form of a BCL2 family protein transcript as compared to the amount of a protein encoded by a shorter alternative splice isoform of the BCL2 family transcript,
indicates a susceptibility of the CSC to a self-renewal pathway inhibitory compound, or a lack of susceptibility of the CSC to a drug or a pro-differentiation compound or drug, or a poorer prognosis for the cancer related to the CSC, or enhanced or increased disease progression, or increased CSC survival and/or increased CSC survival in response to a treatment, diet or therapy;

(b) the method of (a), wherein the BCL2 family transcript comprises or consists of a myeloid cell leukemia sequence 1 (MCL1, or MCL1) transcript;
(c) the method of (a), wherein the BCL2 family transcript comprises or consists of a Bcl-XL (or BCXL, or B-cell lymphoma-extra large) transcript;
(d) the method of (a), wherein the BCL2 family transcript comprises or consists of a BFl1, or a pro-apoptotic BCL2 family member transcript;
(e) the method of any of (a) to (d), wherein the detecting and quantifying the transcript comprises use of PCR;
(f) the method of (e), wherein the PCR comprises a Q-RT-PCR or equivalent;
(g) the method of any of (a) to (e), wherein the method comprises determining the ratio of longer BCL2 family transcript isoforms to shorter BCL2 family transcript isoforms, wherein the detected presence of more of a longer BCL2 family transcript isoform to a shorter BCL2 family transcript isoform indicates a susceptibility of the CSC to a self-renewal pathway inhibitory compound, or a lack of susceptibility of the CSC to a drug or a pro-differentiation compound or drug, or a poorer prognosis for the cancer related to the CSC; or
(h) the method of any of (a) to (g), wherein the cancer stem cell (CSC) is a leukemia stem cell (LSC).

In alternative embodiments, the disclosure herein provides methods for determining whether a CSC in a niche is more pro-apoptotic or more anti-apoptotic in relation to a normal stem cell or a CSC from another niche, comprising:
(a) (i) providing at least one or a plurality of CSCs from a niche;
(ii) detecting and quantifying in the at least one or a plurality of CSCs:
  (1) one or more B-cell lymphoma-2 (BCL2) family protein(s) or protein isoform(s), and/or, a transcript (mRNA, message) encoding one or more BCL2 family protein(s) or protein isoform(s), and
  (2) the cell cycle status or the amount of quiescence, or exit from the cell cycle, of the CSC; and
(iii) comparing (1) the quantified levels of protein or transcript in the CSC to a cell having a comparable normal (wild type) phenotype or a CSC from another niche, or the amount of one protein isoform to a second protein isoform (of the same protein), or the amount of transcript encoding one protein isoform to the amount of transcript encoding a second protein isoform (of the same protein), and (2) the cell cycle status or the amount of quiescence, or exit from the cell cycle, of the CSC comparable to a normal (wild type) CSC or a CSC from another niche;
wherein the combination of
  (1) increased amount of quiescence, or exit from the cell cycle, in the CSC as compared to a cell having a comparable normal (wild type) phenotype or a CSC from another niche, and
  (2) more amount of a longer splice form of a BCL2 family protein transcript as compared to a shorter alternative splice isoform of the BCL2 family transcript, and/or more amount of a protein encoded by a longer splice form of a BCL2 family protein transcript as compared to the amount of a protein encoded by a shorter alternative splice isoform of the BCL2 family transcript,
indicates the CSC in the niche is more pro-apoptotic or more anti-apoptotic in relation to a normal stem cell or a CSC from another niche;

(b) the method of (a), wherein the BCL2 family transcript comprises or consists of a myeloid cell leukemia sequence 1 (MCL1) transcript;
(c) the method of (a), wherein the BCL2 family transcript comprises or consists of a Bcl-XL (B-cell lymphoma-extra large) transcript;
(d) the method of (a), wherein the BCL2 family transcript comprises or consists of a BM, or a pro-apoptotic BCL2 family member transcript;
(e) the method of any of (a) to (d), wherein the detecting and quantifying the transcript comprises use of PCR;
(f) the method of (e), wherein the PCR comprises a Q-RT-PCR or equivalent;
(g) the method of any of (a) to (e), wherein the method comprises determining the ratio of longer BCL2 family transcript isoforms to shorter BCL2 family transcript isoforms, wherein the detected presence of more of a longer BCL2 family transcript isoform to a shorter BCL2 family transcript isoform indicates a susceptibility of the CSC to a self-renewal pathway inhibitory compound, or a lack of susceptibility of the CSC to a drug or a pro-differentiation compound or drug, or a poorer prognosis for the cancer related to the CSC; or
(h) the method of any of (a) to (g), wherein the cancer stem cell (CSC) is a leukemia stem cell (LSC).

In alternative embodiments, the disclosure herein provides methods for determining the prognosis or malignant potential of a cancer, comprising:
(a) (i) providing at least one or a plurality of CSCs, or at least one or a plurality of CSCs from a niche;
(ii) detecting and quantifying in the at least one or a plurality of CSCs:
  (1) one or more B-cell lymphoma-2 (BCL2) family protein(s) or protein isoform(s), and/or, a transcript (mRNA, message) encoding one or more BCL2 family protein(s) or protein isoform(s), and
  (2) the cell cycle status or the amount of quiescence, or exit from the cell cycle, of the CSC; and
(iii) comparing (1) the quantified levels of protein or transcript in the CSC to a cell having a comparable normal (wild type) phenotype or a CSC from another niche, or the amount of one protein isoform to a second protein isoform (of the same protein), or the amount of transcript encoding one protein isoform to the amount of transcript encoding a second protein isoform (of the same protein), and (2) the cell cycle status or the amount of quiescence, or exit from the cell cycle, of the CSC comparable to a normal (wild type) CSC or a CSC from another niche;
wherein the combination of
  (1) increased amount of quiescence, or exit from the cell cycle, in the CSC as compared to a cell having a comparable normal (wild type) phenotype or a CSC from another niche, and
  (2) more amount of a longer splice form of a BCL2 family protein transcript as compared to a shorter alternative splice isoform of the BCL2 family transcript, and/or more amount of a protein encoded by a longer splice form of a BCL2 family protein transcript as compared to the amount of a protein encoded by a shorter alternative splice isoform of the BCL2 family transcript,
indicates a poor or poorer prognosis or increased malignant potential of a cancer, or a poor or poorer prognosis or increased malignant potential of the tumor in the niche;
(b) the method of (a), wherein the BCL2 family transcript comprises or consists of a myeloid cell leukemia sequence 1 (MCL1) transcript;

(c) the method of (a), wherein the BCL2 family transcript comprises or consists of a Bcl-XL (B-cell lymphoma-extra large) transcript;

(d) the method of (a), wherein the BCL2 family transcript comprises or consists of a BFI1, or a pro-apoptotic BCL2 family member transcript;

(e) the method of any of (a) to (d), wherein the detecting and quantifying the transcript comprises use of PCR;

(f) the method of (e), wherein the PCR comprises a Q-RT-PCR or equivalent;

(g) the method of any of (a) to (e), wherein the method comprises determining the ratio of longer BCL2 family transcript isoforms to shorter BCL2 family transcript isoforms, wherein the detected presence of more of a longer BCL2 family transcript isoform to a shorter BCL2 family transcript isoform indicates a susceptibility of the CSC to a self-renewal pathway inhibitory compound, or a lack of susceptibility of the CSC to a drug or a pro-differentiation compound or drug, or a poorer prognosis for the cancer related to the CSC; or (h) the method of any of (a) to (g), wherein the cancer stem cell (CSC) is a leukemia stem cell (LSC).

In alternative embodiments, the disclosure herein provides methods for determining the anti-apoptotic versus a pro-apoptotic potential of a cancer stem cell (CSC), the method comprising:

(a) (i) providing at least one or a plurality of CSCs, or at least one or a plurality of CSCs from a niche;

(ii) detecting and quantifying in the at least one or a plurality of CSCs:

(1) one or more B-cell lymphoma-2 (BCL2) family protein(s) or protein isoform(s), and/or, a transcript (mRNA, message) encoding one or more BCL2 family protein(s) or protein isoform(s), and (2) the cell cycle status or the amount of quiescence, or exit from the cell cycle, of the CSC; and (iii) comparing (1) the quantified levels of protein or transcript in the CSC to a cell having a comparable normal (wild type) phenotype or a CSC from another niche, or the amount of one protein isoform to a second protein isoform (of the same protein), or the amount of transcript encoding one protein isoform to the amount of transcript encoding a second protein isoform (of the same protein), and (2) the cell cycle status or the amount of quiescence, or exit from the cell cycle, of the CSC comparable to a normal (wild type) CSC or a CSC from another niche;

wherein the combination of (1) increased amount of quiescence, or exit from the cell cycle, in the CSC as compared to a cell having a comparable normal (wild type) phenotype or a CSC from another niche, and (2) more amount of a longer splice form of a BCL2 family protein transcript as compared to a shorter alternative splice isoform of the BCL2 family transcript, and/or more amount of a protein encoded by a longer splice form of a BCL2 family protein transcript as compared to the amount of a protein encoded by a shorter alternative splice isoform of the BCL2 family transcript, indicates a pro-apoptotic potential of a cancer stem cell (CSC), or a pro-apoptotic potential of a cancer stem cell (CSC) in the niche;

(b) the method of (a), wherein the BCL2 family transcript comprises or consists of a myeloid cell leukemia sequence 1 (MCL1) transcript;

(c) the method of (a), wherein the BCL2 family transcript comprises or consists of a Bcl-XL (B-cell lymphoma-extra large) transcript;

(d) the method of (a), wherein the BCL2 family transcript comprises or consists of a BFI1, or a pro-apoptotic BCL2 family member transcript;

(e) the method of any of (a) to (d), wherein the detecting and quantifying the transcript comprises use of PCR;

(f) the method of (e), wherein the PCR comprises a Q-RT-PCR or equivalent;

(g) the method of any of (a) to (e), wherein the method comprises determining the ratio of longer BCL2 family transcript isoforms to shorter BCL2 family transcript isoforms, wherein the detected presence of more of a longer BCL2 family transcript isoform to a shorter BCL2 family transcript isoform indicates a susceptibility of the CSC to a self-renewal pathway inhibitory compound, or a lack of susceptibility of the CSC to a drug or a pro-differentiation compound or drug, or a poorer prognosis for the cancer related to the CSC; or (h) the method of any of (a) to (g), wherein the cancer stem cell (CSC) is a leukemia stem cell (LSC).

In alternative embodiments, the disclosure provides a method for treating a subject with a quiescent cancer stem cell (CSC) in a niche comprising:

(a) (i) providing a sample from the subject of at least one or a plurality of CSCs from a niche;

(ii) detecting and quantifying in the at least one or a plurality of CSCs:

(1) one or more B-cell lymphoma-2 (BCL2) family protein(s) or protein isoform(s), and/or, a transcript (mRNA, message) encoding one or more BCL2 family protein(s) or protein isoform(s), and (2) the cell cycle status or the amount of quiescence, or exit from the cell cycle, of the CSC; and (iii) comparing (1) the quantified levels of protein or transcript in the CSC to a cell having a comparable normal (wild type) phenotype or a CSC from another niche, or the amount of one protein isoform to a second protein isoform (of the same protein), or the amount of transcript encoding one protein isoform to the amount of transcript encoding a second protein isoform (of the same protein), and (2) the cell cycle status or the amount of quiescence, or exit from the cell cycle, of the CSC comparable to a normal (wild type) CSC or a CSC from another niche;

wherein the combination of (1) increased amount of quiescence, or exit from the cell cycle, in the CSC as compared to a cell having a comparable normal (wild type) phenotype or a CSC from another niche, and (2) more amount of a longer splice form of a BCL2 family protein transcript as compared to a shorter alternative splice isoform of the BCL2 family transcript, and/or more amount of a protein encoded by a longer splice form of a BCL2 family protein transcript as compared to the amount of a protein encoded by a shorter alternative splice isoform of the BCL2 family transcript, indicates that the subject should be treated with one of more chemotherapeutic agents;

(b) the method of (a), wherein the BCL2 family transcript comprises or consists of a myeloid cell leukemia sequence 1 (MCL1, or MCL1) transcript;

(c) the method of (a), wherein the BCL2 family transcript comprises or consists of a Bcl-XL (or BCXL, or B-cell lymphoma-extra large) transcript;

(d) the method of (a), wherein the BCL2 family transcript comprises or consists of a BFl1, or a pro-apoptotic BCL2 family member transcript;

(e) the method of any of (a) to (d), wherein the detecting and quantifying the transcript comprises use of PCR;

(f) the method of (e), wherein the PCR comprises a Q-RT-PCR or equivalent;

(g) the method of any of (a) to (e), wherein the method comprises determining the ratio of longer BCL2 family transcript isoforms to shorter BCL2 family transcript isoforms, wherein the detected presence of more of a longer BCL2 family transcript isoform to a shorter BCL2 family transcript isoform indicates a susceptibility of the CSC to a self-renewal pathway chemotherapeutic compound; or (h) the method of any of (a) to (g), wherein the cancer stem cell (CSC) is a leukemia stem cell (LSC). In alternative embodiments of the method, the subject is treated with one or more pan-BCL2 inhibitors. In still other embodiments the subject is treated with additional chemotherapeutic agents.

In alternative embodiments, disclosed herein is a method for determining if a subject should be enrolled in a clinical trial comprising:

(a) (i) providing a sample from the subject of at least one or a plurality of CSCs from a niche;

(ii) detecting and quantifying in the at least one or a plurality of CSCs:

(1) one or more B-cell lymphoma-2 (BCL2) family protein (s) or protein isoform(s), and/or, a transcript (mRNA, message) encoding one or more BCL2 family protein(s) or protein isoform(s), and (2) the cell cycle status or the amount of quiescence, or exit from the cell cycle, of the CSC; and (iii) comparing (1) the quantified levels of protein or transcript in the CSC to a cell having a comparable normal (wild type) phenotype or a CSC from another niche, or the amount of one protein isoform to a second protein isoform (of the same protein), or the amount of transcript encoding one protein isoform to the amount of transcript encoding a second protein isoform (of the same protein), and (2) the cell cycle status or the amount of quiescence, or exit from the cell cycle, of the CSC comparable to a normal (wild type) CSC or a CSC from another niche;

wherein the combination of (1) increased amount of quiescence, or exit from the cell cycle, in the CSC as compared to a cell having a comparable normal (wild type) phenotype or a CSC from another niche, and (2) more amount of a longer splice form of a BCL2 family protein transcript as compared to a shorter alternative splice isoform of the BCL2 family transcript, and/or more amount of a protein encoded by a longer splice form of a BCL2 family protein transcript as compared to the amount of a protein encoded by a shorter alternative splice isoform of the BCL2 family transcript, indicates that the subject should be enrolled in a clinical trial;

(b) the method of (a), wherein the BCL2 family transcript comprises or consists of a myeloid cell leukemia sequence 1 (MCL1, or MCL1) transcript;

(c) the method of (a), wherein the BCL2 family transcript comprises or consists of a Bcl-XL (or BCXL, or B-cell lymphoma-extra large) transcript;

(d) the method of (a), wherein the BCL2 family transcript comprises or consists of a BFl1, or a pro-apoptotic BCL2 family member transcript;

(e) the method of any of (a) to (d), wherein the detecting and quantifying the transcript comprises use of PCR;

(f) the method of (e), wherein the PCR comprises a Q-RT-PCR or equivalent;

(g) the method of any of (a) to (e), wherein the method comprises determining the ratio of longer BCL2 family transcript isoforms to shorter BCL2 family transcript isoforms, wherein the detected presence of more of a longer BCL2 family transcript isoform to a shorter BCL2 family transcript isoform indicates a susceptibility of the CSC to a self-renewal pathway chemotherapeutic compound; or (h) the method of any of (a) to (g), wherein the cancer stem cell (CSC) is a leukemia stem cell (LSC).

In alternative embodiments, disclosed herein are methods for sensitizing a quiescent cancer stem cell in a niche comprising administering to a subject in need of treatment a compound that invokes cycling of a dormant cancer stem cell which results in sensitizing the cancer stem cells to a chemotherapeutic agent. In other aspects of this embodiment, the compound that invokes cycling is an inhibitor of a pathway involved with quiescence of a cancer stem cell. In still other embodiments, the pathway involved with quiescence is a pathway involved with apoptosis. In alternative embodiments the pathway involves isoforms of BLC2. In alternative embodiments, the compound that invokes cycling is one or more pan-BCL2 inhibitors. In still other embodiments of this method, cancer stem cells are sensitized to a tyrosine kinase inhibitor, such as a tyrosine kinase that inhibits BCR-ABL.

The details of one or more embodiments of the disclosure are set forth in the accompanying drawings and the description below. Other features, objects, and advantages of the disclosure herein will be apparent from the description and drawings, and from the claims.

All publications, patents, patent applications cited herein are hereby expressly incorporated by reference for all purposes.

BRIEF DESCRIPTION OF THE DRAWINGS

FIG. 4(b) graphically illustrates: representative FACS plots showing gating and cell-cycle analysis of live (propidium iodide negative [PI-]), bone marrow-engrafted BC progenitors (CD45$^{32}$CD34$^-$CD38$^-$Lin$^-$); FMO gating controls are shown in the top row, and engrafted bone marrow is shown in the bottom row, FIG. 4(c) graphically illustrates: quantification of BC progenitors in untreated marrow in the different phases of cell cycle G0, G1 and G2/S/M; n=10 engrafted bones, graph shows mean ±SEM, FIG. 4(d)-(e) illustrated images of histological analysis of engrafted bone marrow showing hematoxylin and eosin (H&E), human CD34, CD38 and Ki67, and pHis-H3 staining, the dotted lines delineate the endosteum (50 micrometers from the bone edge);

FIG. 4(e) illustrates images of a histical analysis of engrafted bone marrow showing hematoxylin and eosin (H&E), human CD34, CD38 and Ki67, and pHis-H3 staining. The dotted lines delineate the endosteum (approximately 50 mm from the bone edge); All scale bars equal 50µm.

DETAILED DESCRIPTION OF THE EMBODIMENTS

Figure 1:
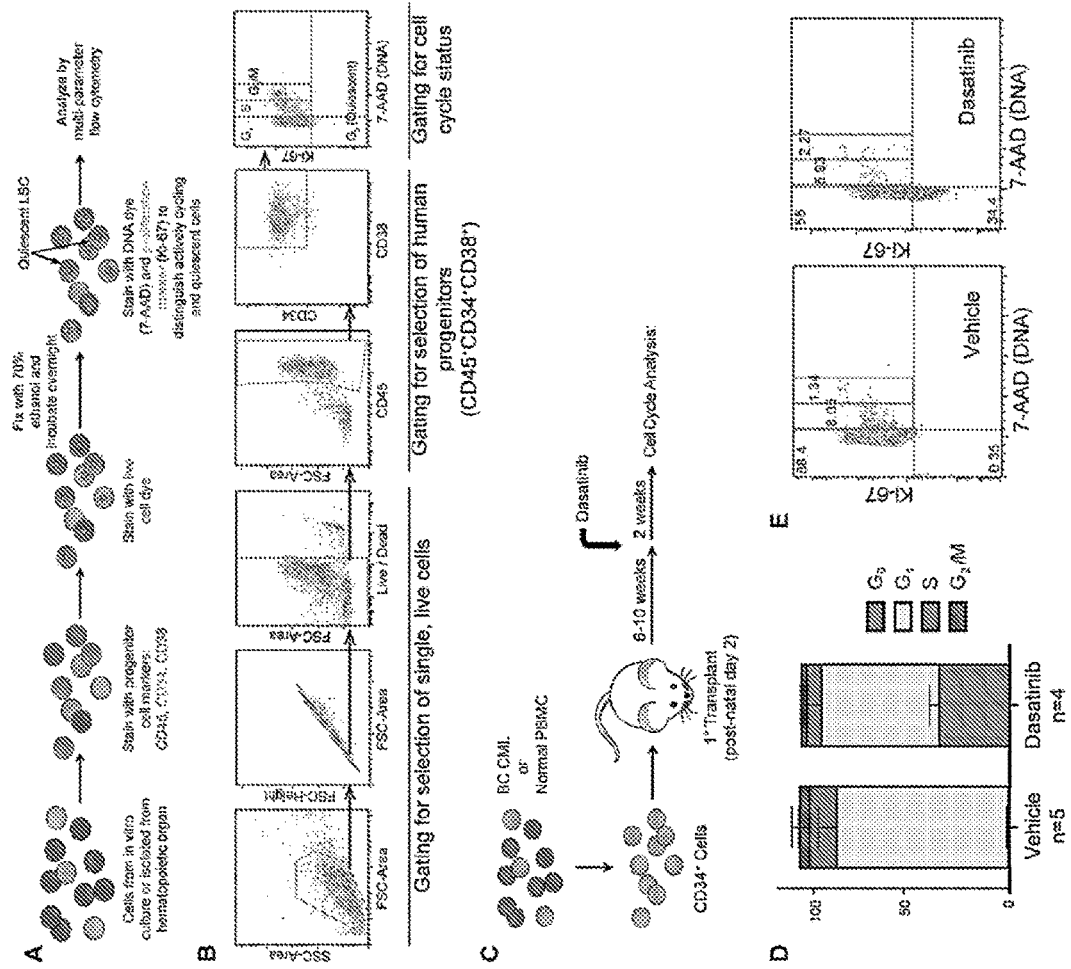
FIG. 1 Method to analyze cell cycle of LSC from tumor niches. (A) Experimental design. (B) Gating strategy for cell cycle analysis of bonce marrow engrafted blast crisis chronic myeloid leukemia cells (BC CML); (C) In vivo experimental design. Human BC CML $CD34^+$ cells are transplanted into neonatal mice. Engrafted mice were treated daily with 25 mg/kg dasatinib (oral) or vehicle, sacrificed after 2 weeks of treatment and bone marrow was analyzed for cell cycle status. (D) graphically illustrates: Cell cycle analysis of bone marrow engrafted BC CML cells using Ki-67 and 7-AAD to differentiate between G0, G1, S and G2/M cells. $CD45^+CD34^+CD38^+$ cells were quantified for each sub-group in the marrow of vehicle (n=5) and dasatinib (n=4) treated mice. Graph shows mean+/−SEM. (E) Representative flow cytometry plots of BC CML CSC in the bone marrow of vehicle (left) and dasatinib-treated mice right.

Disclosed herein are methods for identifying and treating subjects with quiescent cancer stem cells by targeting cancer stem cell niches, such as bone marrow, wherein if a subject is determined to have a niche specific quiescent cancer stem cell as disclosed herein the patient is treated and/or enrolled in a clinical trial. The methods disclosed herein are based on the studies disclosed herein which show that niche dependent pro-survival BCL2 family gene isoform expression promotes malignant reprograming of myeloid progenitors into self-renewing blast crisis (BC) cancer stem cells that become quiescent in the marrow niche and contribute to BC transformation as well as tyrosine kinase inhibitor (TKI) resistance. The methods disclosed herein are applicable to any cancer associated with quiescent cancer stem cells found in a niche such as marrow and associated with BCL2 pro-survival isoform expression, such as, without limitation, myeloproliferative neoplasm, myelodysplastic syndrome, acute myeloid leukemia (AML), acute lymphocytic leukemia (ALL), chronic lymphocytic leukemia (CLL), chronic myeloid leukemia blast crisis, Burkitt lymphoma, diffuse large B-Cell lymphoma, Ewing sarcoma, follicular lymphoma, gastrointestinal stromal tumor, hepatocellular carcinoma, mantle cell lymphoma, multiple myeloma, neuroblastoma, non-small cell lung cancer, ovarian cancer, small cell lung carcinoma, T-cell leukemia/lymphoma, breast cancer, colon cancer, melanoma, head and neck cancer and prostate cancer.

As used herein, the term "subject" refers to an animal, typically a human (i.e., a male or female of any age group, e.g., a pediatric patient (e.g., infant, child, adolescent) or adult patient (e.g., young adult, middle-aged adult or senior adult) or other mammal, such as a primate (e.g., cynomolgus monkey, rhesus monkey); other mammals such as rodents (mice, rats), cattle, pigs, horses, sheep, goats, cats, dogs; and/or birds, that will be or has been the object of treatment, observation, and/or experiment. When the term is used in conjunction with administration of an, agent, composition, compound or drug, then the patient has been the object of treatment, observation, and/or administration of the composition, compound or drug.

As used herein, the terms "compositions," "drug," "agent," "compound," and "therapeutic agent" are used interchangeably, and may include, without limitation, small molecule compounds, biologics (e.g., antibodies, proteins, protein fragments, fusion proteins, glycoproteins, etc.), nucleic acid agents (e.g., antisense, RNAi/siRNA, and microRNA molecules, etc.), vaccines, etc., which may be used for therapeutic and/or preventive treatment of a disease (e.g., malignancy).

A "chemotherapeutic agent" is a compound useful in the treatment of cancer regardless of mechanism of action. Chemotherapeutic agents include compounds used in "targeted therapy" and conventional chemotherapy.

Chemotherapeutic agents useful for the methods disclosed herein include, without limitation pan-BCL2 inhibitors such as, without limitation, ABT-737, ABT-263, EGCG, AT-101, BI79D10, Sabutoclax (BI-97C1), Apogossypolone, "compound 21", S1, B-11, TW-37, Gossypol, Apogossypol, A-385358, Obatoclax (G15-070), BH3I-1, HA14-1, WL-276, YC137, Antimycin A, Chelerythrine, Maritoclax (Marinopyrrole), BH3-M6 and combinations thereof.

Other chemotherapeutic agents useful for the invention disclosed herein include dasatinib, imatinib, bafetinib, bosutinib, nilotinib, and AP24534.

Examples of additional chemotherapeutic agents that may be useful for treating a subject found to have a quiescent niche specific cancer stem cell as described herein include Erlotinib (TARCEVA®., Genentech/OSI Pharm.), Bortezomib (VELCADE®., Millennium Pharm.), Fulvestrant (FASLODEX®., AstraZeneca), Sutent (SU11248, Pfizer), Letrozole (FEMARA®., Novartis), PTK787/ZK 222584 (Novartis), Oxaliplatin (Eloxatin®., Sanofi), 5-FU (5-fluorouracil), Leucovorin, Rapamycin (Sirolimus, RAPAMUNE®., Wyeth), Lapatinib (TYKERB®., GSK572016, Glaxo Smith Kline), Lonafarnib (SCH 66336), Sorafenib (BAY43-9006, Bayer Labs), Irinotecan (CAMPTOSAR®, Pfizer) and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, bendamustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega11 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK®polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™. (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

The chemotherapeutic agents listed herein can be given in combination with each other as well as in combination with radiation treatments and radioactively labeled cancer agents.

Steroids used alone or in combination with a clinically employed cancer regimen are also considered drugs that can be used alone or combined the chemotherapeutic agents listed herein.

The disclosure herein provides compositions and methods to determine the self-renewal potential of cancer stem cells (CSCs) through analysis of both the differential expression of BCL2 family molecules, such as alternatively spliced forms of BCL2 family molecules, and cell cycle status of a CSC. In alternative embodiments, the disclosure provides methods that compare both cell cycle status and differential expression of BCL2 family molecules, such as alternatively spliced forms of BCL2 family molecules to determine whether or not CSC in bone and bone marrow niches are susceptible or resistant to treatment. In one embodiment, detection of increased quiescence (exit from the cell cycle) of CSC in the niche in combination with aberrant ratios of BCL2 family isoforms, e.g., long isoforms of BCL2 family members such as MCL1, BCLX and BFI1, are associated with disease progression, increased CSC survival and/or increased CSC survival in response to a treatment, diet or therapy and the like.

A "niche" for a cancer stem cell is the microenvironment which controls, e.g., properties of the cancer stem cell, such as, without limitation, self-renewal, apoptosis resistance, and differentiation. The niche may also provide protection to cancer stem cells and contribute to their resistance to therapy. Examples of niches for cancer stem cells include, without limitation, bone marrow, and the intestinal crypt for colon cancer. A discussion of cancer stem cell niches can be found in Lander et al. *BMC Biology* (2012), 10-19 and Melo et al., *Cancer Research* (2011) 71:634-639. Both are incorporated by reference herein in their entireties.

In alternative embodiments, the disclosure provides methods for characterization of both cell cycle status and differential expression of BCL2 family molecules in both CSC in specific tumor niches and normal stem cells. In alternative embodiments, the disclosure provides methods for characterization of both cell cycle status and differential expression of BCL2 family molecules in both CSC in specific tumor niches and normal stem cells over the course of treatment to e.g., allow for prediction of the drug susceptibility of CSCs, determination of cancer prognosis and progression and monitoring of CSC response to anticancer therapeutics.

In alternative embodiments, the disclosure provides methods for characterizing cancer stem cells (CSCs) within a tumor niche, e.g., a bone marrow niche, and to prognosticate and determine the response of cancer stem cells (CSCs) to anticancer therapies, treatments, diets and the like. In alternative embodiments, methods of disclosed herein comprise determining cell cycle status of CSC in a tumor niche, quantifying (quantification) of BCL2 family molecule population ratios, e.g., BCL2 family mRNA splice isoform ratios (e.g., in MCL1, BCLX and BFI1 isoforms), in the CSC population; and using both as a "collective" marker of cell survival within tumor niches. In alternative embodiments, methods disclosed herein comprise comparing (comparison) of the CSC cell cycle status and BCL2 mRNA isoform ratios between CSCs and normal stem cells, and within CSCs over the course of treatment, therapy, diet and the like. In alternative embodiments, methods disclosed herein comprise predicting (prediction) of CSC drug or treatment susceptibility, determination of cancer prognosis, and progression and monitoring of CSC response to anticancer therapeutics, treatments, diets and the like.

In alternative embodiments, the disclosure provides methods for predicting cancer progression, drug susceptibility and cancer response to a treatment, diet or therapy by analyzing both: (1) the differential expression of BCL2 family molecules, such as alternatively spliced forms of BCL2 family molecules, and (2) cell cycle status of CSC of the cancer. Thus, methods disclosed herein take into account the heterogeneity of most tumors by: specifically examining CSC, which drive the progression and relapse of cancer; and examining the effects of cell cycle status within a tumor niche on CSC survival and response to a treatment, diet or therapy and the like.

In alternative embodiments, methods disclosed herein comprise use of flow cytometric, amplification assays (e.g., polymerase chain reaction, or PCR; or qPCR, or real-time polymerase chain reaction, also called quantitative real time polymerase chain reaction (Q-PCR/qPCR/qrt-PCR) or kinetic polymerase chain reaction (KPCR)), immunocytochemistry techniques, chromatography (e.g., HPLC) and the like to characterize BCL2 family molecule status, including spliced mRNA populations, protein expression from these spliced mRNA populations, and cell cycle status. In alternative embodiments, methods disclosed herein examine the CSC population specifically. In alternative embodiments, methods disclosed herein distinguish between different tumor niches. In alternative embodiments, methods disclosed herein quantify cell cycle status and BCL2 family member isoform mRNA expression in CSC, including CSC from different tumor niches.

In one embodiment, characterization of a CSC cell cycle comprises use of a rapid flow cytometry-based analysis. Peripheral blood mononuclear cells (PBMCs) are harvested from leukemic blood and bone marrow samples. The PBMCs are run through a CD34-selection column and are then surface stained with fluorescence-conjugated antibodies to CSC markers. The cells are fixed overnight, permeabilized and finally stained intracellularly with fluorescence-conjugated antibodies to Ki-67 and a fluorescent chemical with strong affinity for DNA. The stained cells are analyzed on a flow cytometer and the $CD34^+CD38^+$ staining fraction is analyzed for cell cycle status, see FIG. 1.

As used herein "sample" refers to any patient sample, including but not limited to a fluid, cell or tissue sample that comprises cancer cells isolated from a niche, such as marrow, suspected to contain quiescent cancer stem cells. The sample includes, for example, a blood sample, a fractionated blood sample, a bone marrow sample, a biopsy, a frozen tissue sample, a fresh tissue specimen, a cell sample, and/or a paraffin embedded section, that can be used to determine if the sample contains, without limitation, quiescent a cancer stem cell, and the presence of BCL2 isoform family members associated with pro-survival. Preferably, the sample is obtained from a suspected niche for cancer stem cells, e.g., without limitation, bone marrow, and/or intestinal crypt.

In one embodiment, in addition to cell cycle status, expression of BCL2 isoform expression is quantified; their combination are a marker, or prognostic, of CSC survival in an individual, e.g., in a niche environment. In alternative embodiments, polymerase chain reaction, or PCR; or qPCR, or real-time polymerase chain reaction, also called quantitative real time polymerase chain reaction (Q-PCR/qPCR/qrt-PCR) or kinetic polymerase chain reaction (KPCR), is used with e.g., splice isoform-specific primers and/or whole transcriptome sequencing. The quantification can be used to determine the splice isoform ratio in CSC from different niches to determine whether CSC are more pro-apoptotic or more anti-apoptotic in relation to normal stem cells or CSC from other niches.

Figure 2:
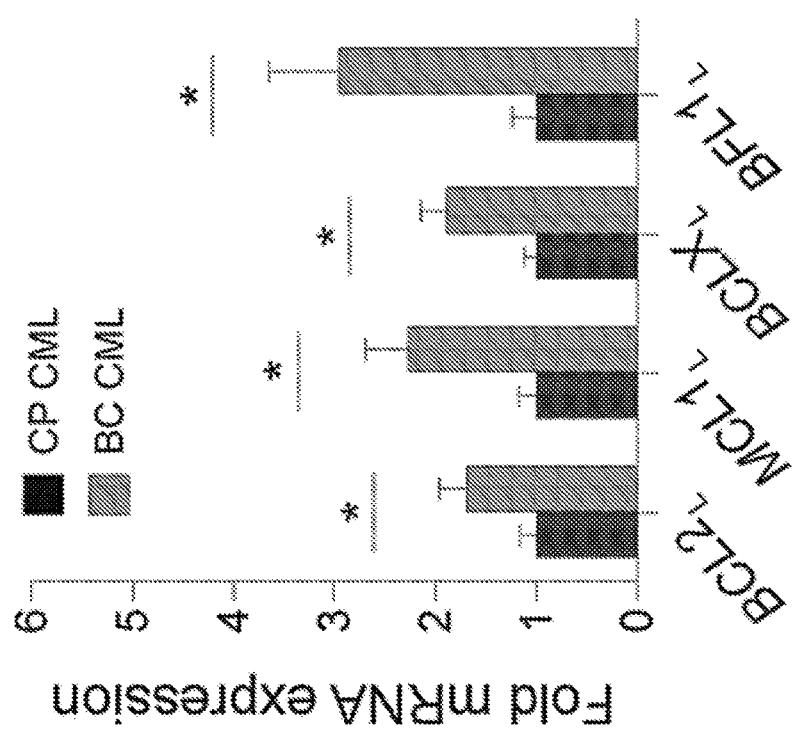
FIG. 2 graphically illustrates: qRT-PCR of pro-survival (long isoforms) BCL2, MCL1, BCLX and BFL1 mRNAs in FACS sorted $CD34^+CD38^+lin^-PI-$ cells (progenitors) from primary CP CML (black, n=13) and BC CML (gray, n=11) samples. Values are normalized to human HPRT mRNA expression. Graphs show mean+/−SEM; *$p<0.05$ by unpaired t-test.

Disclosed herein is an optimized method to determine the cell cycle status of CSC from multiple tumor niches and compared the effects of various chemotherapies on cell cycle status, e.g., as illustrated in FIG. 1. We characterized the splice isoform expression pattern of four BCL2 family members in CSC from blast crisis chronic myeloid leukemia (CML) and observed a statistically significant increase in the expression of the long isoforms of BCL2, MCL1, BCLX and BFl1 with disease progression, e.g., as illustrated in FIG. 2.

Figure 3:
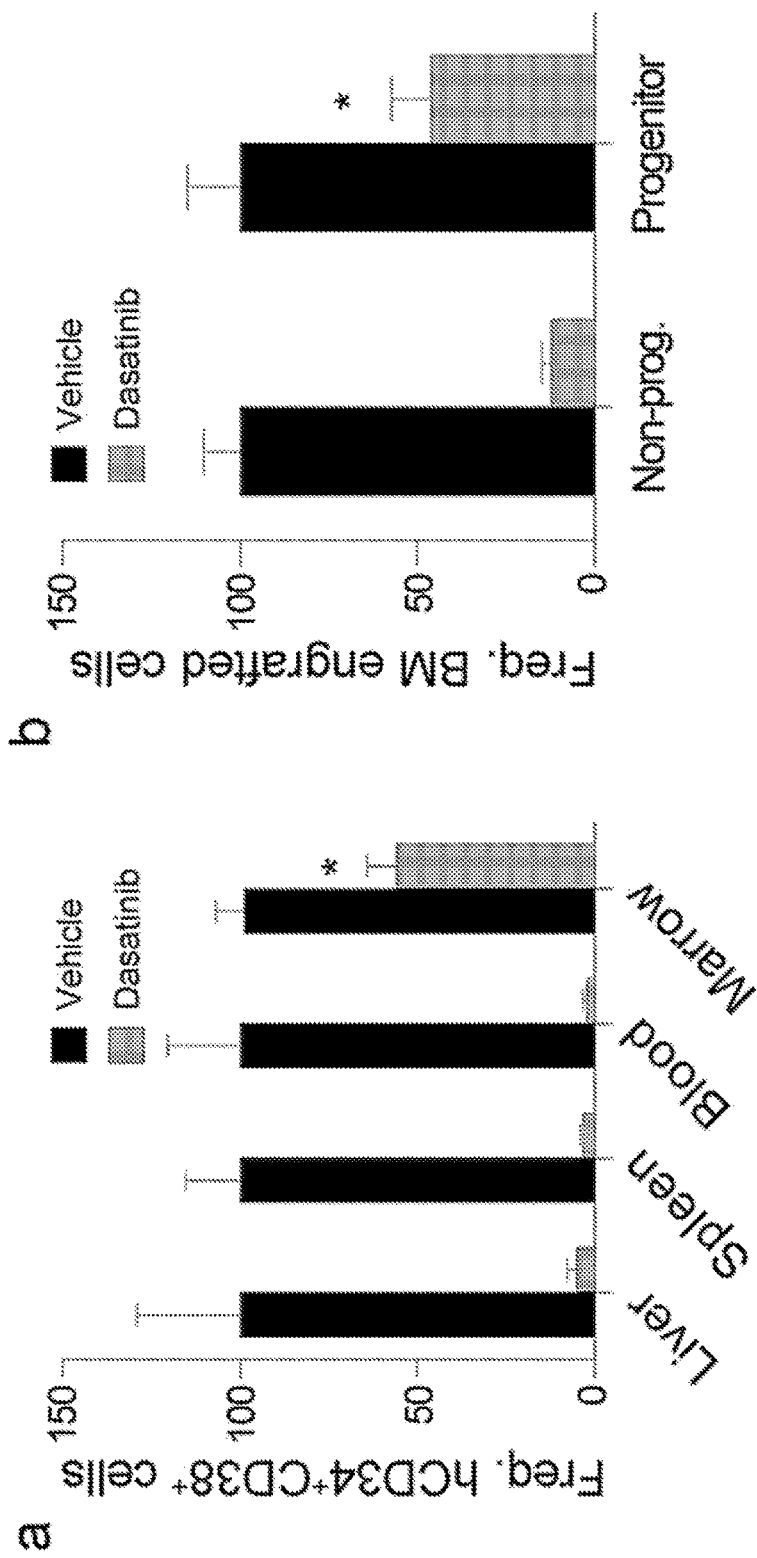
FIG. 3 (a) graphically illustrates: FACS analysis of human BC progenitor engraftment in mouse liver (n=11), spleen (n=11), blood (n=4) and bone marrow (n=12) following treatment with vehicle (black) or dasatinib (grey). All values are normalized to vehicle mean. Statistical analysis is shown for the residual engraftment in bone marrow versus the other tissues (grey bars) by Kruskal-Wallis test with post-hoc analysis; *p<0.05. (b) graphically illustrates: FACS analysis comparing bone marrow engraftment of BC CML progenitors and non-progenitors (CD45$^+$CD34$^-$) following vehicle (black, n=11) or dasatinib (grey, n=11) treatment. All values are normalized to vehicle treated. Statistical analysis is shown for residual engraftment of each population (grey bars) by Mann Whitney test; *p<0.05.
Figure 4:
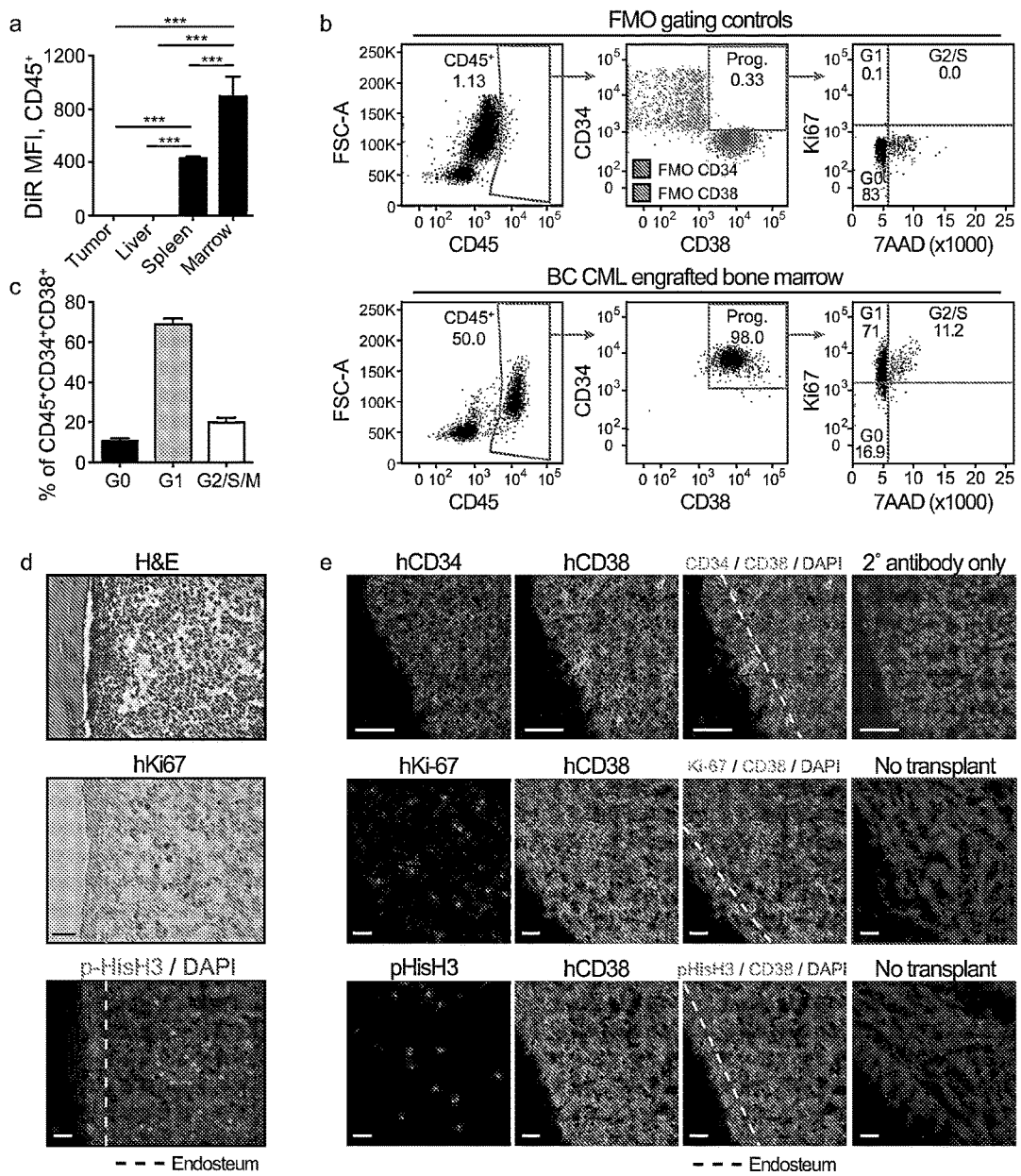
FIG. 4 (a) graphically illustrates: retained DiR fluorescence of BC progenitors (CD45$^+$CD34$^+$CD38$^+$Lin$^-$) engrafted in tumor (n=4), liver (n=4), spleen (n=3), and bone marrow (n=2) 18 weeks after DiR surface straining and transplant. Graph shows mean ±SEM;***, p<0.001 by ANOVA and Tukey post hoc analysis.
Figure 5:
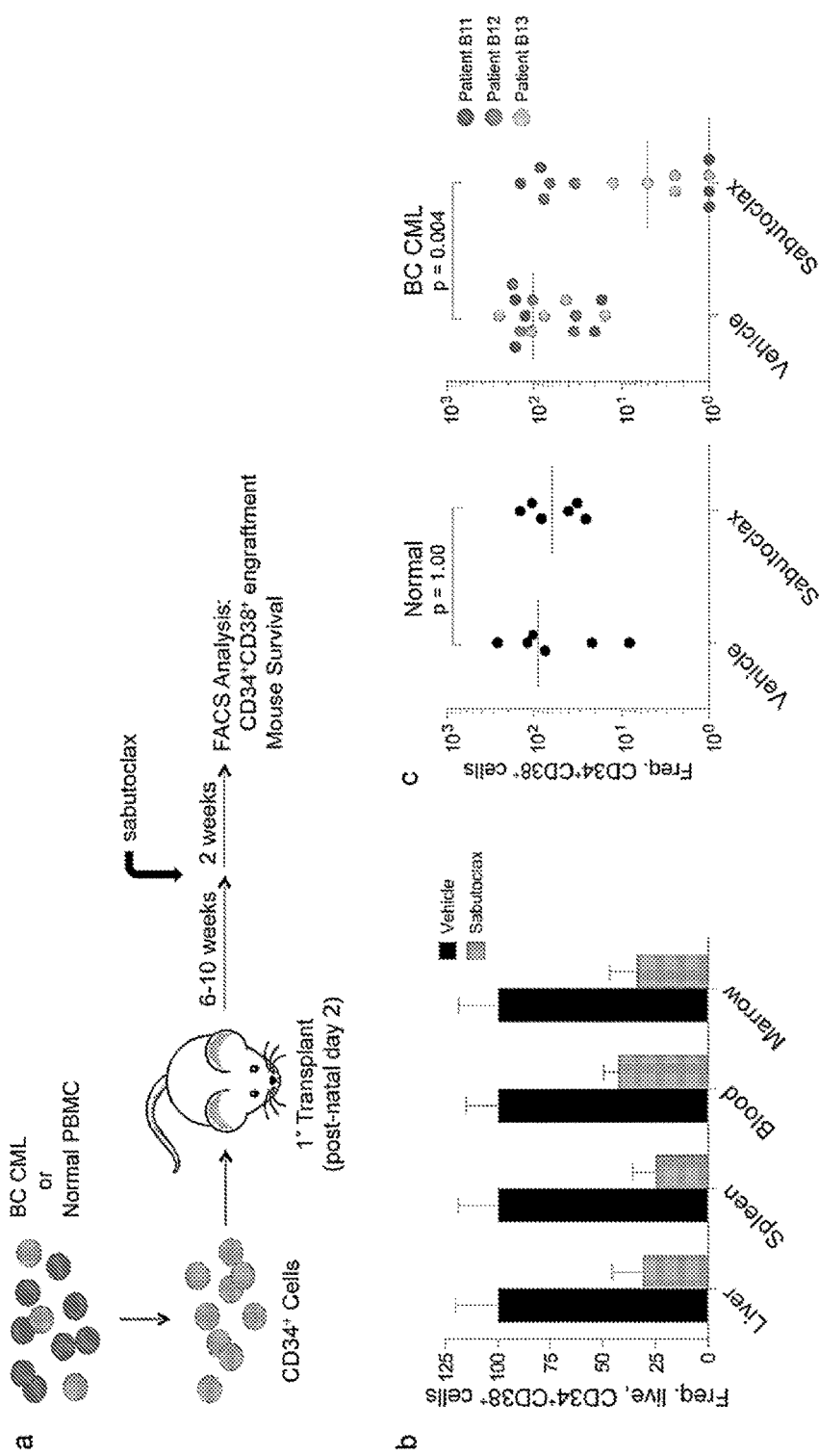
FIG. 5 (a) In vivo experimental design used in the present studies. (b) FACS analysis of BC CML progenitor engraftment in mouse liver, spleen, blood and bone marrow following treatment with vehicle (n=15) or sabutoclax (n=13). All values are normalized to vehicle mean. (c) FACS analysis of bone marrow engrafted progenitors following treatment with vehicle or sabutoclax: Left) Engraftment of normal progenitors in vehicle (n=6) and sabutoclax (n=6) treated mice. Right) Engraftment of BC CML progenitors in vehicle (n=15) and sabutoclax (n=13) treated mice. Individual mice are color-coded to indicate the origin of each BC CML transplant. All values are normalized to vehicle treated. Both graphs show median and statistical analysis by Mann Whitney test.
Figure 6:
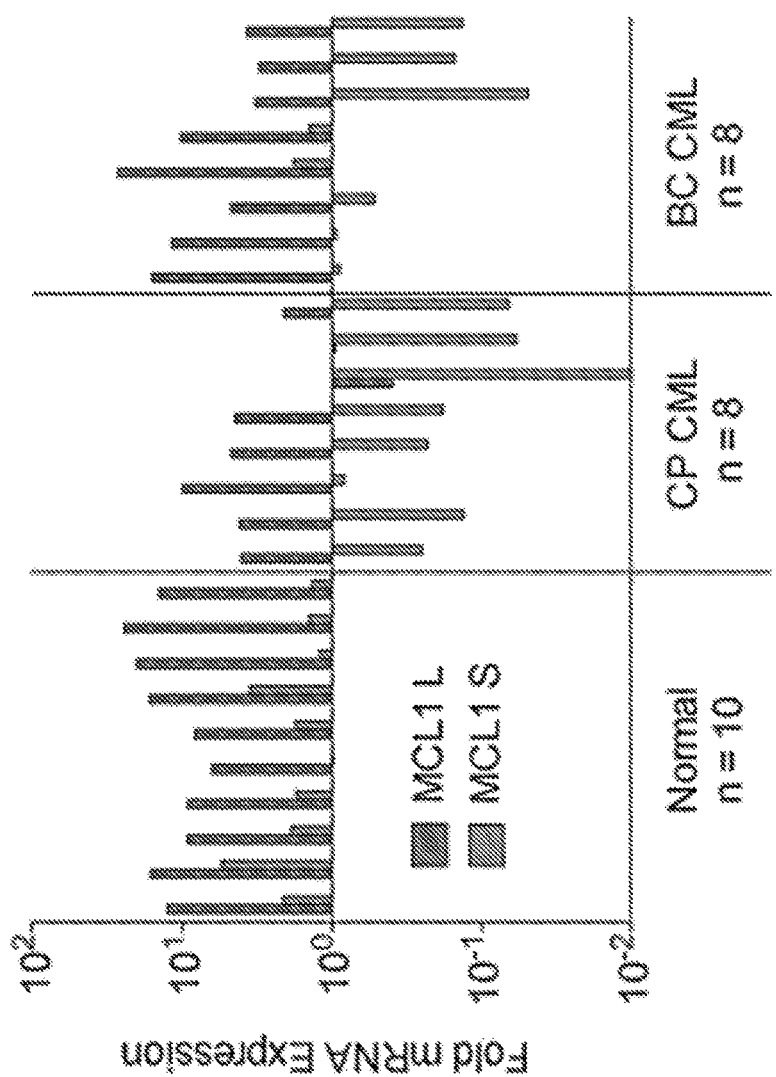
FIG. 6 qRT-PCR of pro-survival (long isoforms) and pro-apoptotic (short isoforms) MCL1 mRNAs in FACS sorted CD34$^+$CD38$^+$lin$^-$PI$^-$ cells (progenitors) from normal human cord blood (n=10), primary CP CML (n=8) and primary BC CML (n=8) samples. Values are normalized to human HPRT mRNA expression.
Figure 7:
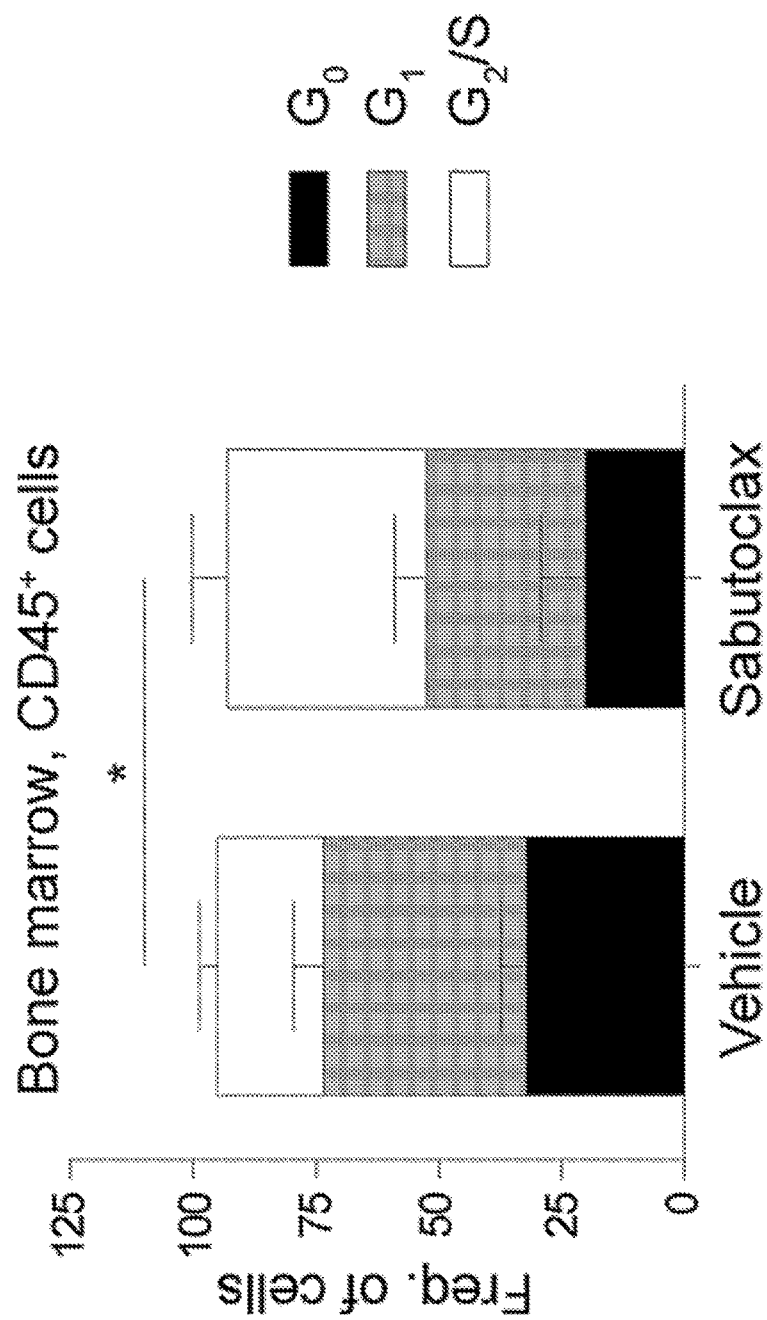
FIG. 7 Cell cycle analysis of bone marrow engrafted BC CML cells using Ki-67 and 7-AAD to differentiate between G0, G1, and G2/S cells. CD45$^+$ cells were quantified for each sub-group in the marrow of vehicle (n=6) and sabutoclax (n=5) treated mice. Graph shows mean+/−SEM. *p<0.05 by unpaired t-test.

We have also demonstrated that tumor niche is important in determining the response of CSC to therapies. CSC in the bone marrow niche are resistant to chemotherapy, as illustrated in FIG. 3 and this may be due to increased quiescence (reduced cell cycling) of the CSC population, as illustrated in FIG. 4. By targeting BCL2 family members with a pan-BCL2 inhibitor (sabutoclax), we have shown that survival of CSC in the protective bone marrow niche is impaired, as illustrated in FIG. 5 and this response to therapy could be monitored by BCL2 family member splice isoform expression (as illustrated in FIG. 6) and/or cell cycle status (as illustrated in FIG. 7).

In alternative embodiments, methods disclosed herein determine the cell cycle status and BCL2 family splice isoform expression within a tumor niche environment prior to and following treatment; in alternative embodiments this is used prognostically to predict tumor, e.g., leukemia, progression, and in alternative embodiments is used to predict whether the CSCs will be susceptible to certain therapeutic drugs, as well as to monitor treatment response. In alternative embodiments, methods disclosed herein are used to evaluate CSC cell cycle status and survival in tumor niches in a number of malignancies, including CML.

While the disclosure herein is not limited by any particular mechanism of action, this disclosure characterizes how CML CSC deregulate apoptosis pathways by differential expression of BCL2 family molecules, and that these changes contribute to CSC ability to survive serial transplantation; and alternatively, this disclosure describes the relationship between isoforms of BCL2 family members and the balance of pro-apoptotic and anti-apoptotic signals in cancer and CSC cells.

In one embodiment, the methods comprise quantification of at least one, several or all of the following: one or more B-cell lymphoma-2 (BCL2) family protein(s) or protein isoform(s); or (2) a transcript (mRNA, message) encoding one or more BCL2 family protein(s) or protein isoform(s).

In one embodiment, an alternatively or aberrantly spliced BCL2 transcript is detected and measure, e.g., the amount of longer versus shorter BCL2 transcripts are detected and quantified. For example, in one embodiment, the presence of longer versus shorter BCL2 splice isoforms is predictive of enhanced self-renewal potential of a CSC. BCL2 messages (transcripts), including alternatively or aberrantly spliced BCL2 message (transcript) isoforms, can be detected and/or quantified by PCR, e.g., by splice isoform specific Q-RT-PCR. In one embodiment, the methods comprise quantification of any one, several or all of these markers BCL2 splice isoform(s).

In one embodiment, methods of the invention are used to predict increased self-renewal of a CSC, and its capacity to be inhibited by targeted self-renewal pathway inhibitors. In alternative embodiments, these exemplary methods allow for determination of a CSC cell's self-renewal state and allow for prediction of the drugability (e.g., susceptibility to a drug) of a CSC, and the progression of the corresponding cancer. For example, in one embodiment, detection and quantifying that the cell contains more of the longer splice isoform of a BCL2 message (transcript) than a shorter splice isoform of the BCL2 message (transcript) (together with cell cycle status, e.g., levels of quiescence) is predictive of an increased CSC cell self-renewal state, i.e., predictive of an enhanced self-renewal potential of a CSC.

While the invention is not limited by any particular mechanism of action, compositions and methods of the invention can predict increased self-renewal of a CSC and its capacity to be inhibited by targeted self-renewal pathway inhibitors because the levels of the longer splice isoform of a BCL2 message (transcript, mRNA) in a cell, together with cell cycle status, e.g., levels of quiescence, can determine or predict whether that cell is susceptible to self-renewal pathway inhibitory drugs; thus, the characterization of BCL2 message (transcript, mRNA) expression and cell cycle status allows for prediction of the drug-susceptibility of CSCs.

With respect to the quantification of BCL2 family mRNAs, methods of the invention can detect and/or differentiate between all of the isoforms of a particular gene or message, e.g., all of the isoforms of a BCL2 family gene and/or mRNA isoform. By detecting and differentiating between all of the isoforms of a particular gene or message, rather than the total amount of only one splice isoform, e.g., a longer BCL2 splice isoform or a shorter BCL2 family member splice isoform (which would not necessarily correspond to the self-renewal state of the cell), the invention by measuring both longer and shorter isoforms (or all of several possible alternatively spliced isoforms that are present at one time in a cell) can better determine whether there are changes in the balance of pro-self-renewal (anti-differentiation) and pro-differentiation signals.

In one embodiment, methods of the invention are used to detect and/or differentiate all of several possible alternatively spliced BCL2 isoform family molecules; e.g., for MCL1 a longer gene product (isoform 1) can enhance cell survival by inhibiting apoptosis while the alternatively spliced shorter gene product (isoform 2) can promote apoptosis and is death-inducing. In one embodiment molecular cross-talk between alternatively spliced BCL2 isoform family molecules and other proteins involved in cell cycle and/or apoptosis are determined.

In alternative embodiments, compositions and methods of the invention can use any flow cytometry method, any PCR and/or any immunohistochemistry technique to characterize the molecular expression, e.g., splice isoform populations or whole transcription determination, in a cancer cell, e.g., in a leukemia cells or in a CSC population. In alternative embodiments, methods of the invention focus on detecting and quantifying BCL2 isoform family expression changes in a CSC population.

In one embodiment, methods of the invention quantify protein, e.g., a BCL2 isoform family protein, in CSC by flow cytometry, e.g., FACS, e.g., a rapid FACS-based analysis. In one embodiment, peripheral blood mononuclear cells (PBMCs) are harvested from leukemic blood or bone marrow samples. In one embodiment PBMCs are run through a CD34 selection column and are then surface stained with fluorescence-conjugated antibodies. In one embodiment cells are fixed with paraformaldehyde, permeabilized with saponin, and finally stained intracellularly with fluorescence-conjugated antibodies to detect BCL2 family proteins. The stained cells are run on a FACS Aria cell sorter and the $CD34^+CD38^+lineage^-$ staining fraction is analyzed for BCL2 family protein expression.

In one embodiment, methods of the invention quantify message (mRNA) using PCR, e.g., using qPCR, using splice isoform-specific primers to quantitate the amount of splice isoforms of BCL2 family proteins. In one embodiment, the quantitation is then used to determine the splice isoform ratio which gives a relative determination of whether cells are more pro-apoptotic or more anti-apoptotic. In alternative embodiments, mRNA quantification using qPCR and splice isoform-specific primers to quantitate the amount of splice isoforms of BCL2 family proteins allows quantitation and determination of the long BCL2 (e.g., MCL1) transcript versus short BCL2 (e.g., MCL1) transcript splice isoform ratio which gives a relative determination of whether cells are more pro-apoptotic or more anti-apoptotic In one embodiment methods of this invention are used to determine and measure the level of BCL2 (e.g., MCL1) isoform family proteins and transcript ratios in CSCs for prognostic reasons, e.g., to predict cancer progression and/or to predict whether the CSCs will be susceptible to certain therapeutic drugs. In one embodiment, the compositions and methods of this invention are applicable to CSCs in a number of malignancies including CML.

Polypeptides and Peptides

In alternative embodiments, the invention provides methods to determine and measure the levels of BCL2 (e.g., MCL1) family proteins and transcripts, and/or BCL2 (e.g., MCL1) family protein and transcript ratios in stem cells, e.g., CSCs, for diagnostic, drug discovery and prognostic reasons.

Polypeptides and peptides used to practice the invention (e.g., as controls, to raise antibodies to BCL2 (e.g., MCL1) family proteins) can comprise a recombinant protein, a synthetic protein, a peptidomimetic, a non-natural peptide, or a combination thereof. Peptides and proteins used to practice the invention can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) *Nucleic Acids Res. Symp. Ser.* 215-223; Horn (1980) *Nucleic Acids Res. Symp. Ser.* 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) *Science* 269:202; Merrifield (1997) *Methods Enzymol.* 289:3-13) including any automated polypeptide synthesis process known in the art.

Antibodies

In alternative embodiments, methods of the invention comprise use of antibodies to determine and measure the levels of BCL2 (e.g., MCL1) family proteins and transcripts, and/or BCL2 (e.g., MCL1) family protein and transcript ratios in stem cells, e.g., CSCs, for diagnostic, drug discovery and prognostic reasons.

In alternative aspects, an antibody for practicing the invention can comprise a peptide or polypeptide derived from, modeled after or substantially encoded by a BCL2 family protein, or immunogenic fragments thereof, capable of specifically binding an antigen or epitope, see, e.g. *Fundamental Immunology*, Third Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. In alternative aspects, an antibody for practicing the invention includes antigen-binding portions, i.e., "antigen binding sites," (e.g., fragments, subsequences, complementarity determining regions (CDRs)) that retain capacity to bind antigen (e.g., a BCL2 family protein, or immunogenic fragments thereof) including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, *CURRENT PROTOCOLS IN IMMUNOLOGY*, Wiley/Greene, NY (1991); Stites (eds.) *BASIC AND CLINICAL IMMUNOLOGY* (7th ed.) Lange Medical Publications, Los Altos, Calif. ("Stites"); Goding, *MONOCLONAL ANTIBODIES: PRINCIPLES AND PRACTICE* (2d ed.) Academic Press, New York, N.Y. (1986); Kohler (1975) *Nature* 256:495; Harlow (1988) *ANTIBODIES, A LABORATORY MANUAL*, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) *Trends Biotechnol.* 15:62-70; Katz (1997) *Annu. Rev. Biophys. Biomol. Struct.* 26:27-45.

In alternative embodiments, antibodies used to practice this invention comprise "affinity matured" antibodies, e.g., antibodies comprising with one or more alterations in one or more hypervariable regions which result in an improvement in the affinity of the antibody for antigen; e.g., a BCL2 (e.g., MCL1) family protein, or immunogenic fragments thereof. In alternative embodiments, antibodies used to practice this invention are matured antibodies having nanomolar or even picomolar affinities for the target antigen, e.g., a targeted transcriptional activating factor. Affinity matured antibodies can be produced by procedures known in the art.

Generating and Manipulating Nucleic Acids

In alternative embodiments, methods of the invention use nucleic acids for detecting and quantifying levels of a transcript (mRNA, message) of a BCL2 (e.g., MCL1) transcript splice isoform. In alternative embodiments, a method of the invention uses nucleic acids for detecting and quantifying levels of a transcript (mRNA, message) of a longer mRNA splice isoform versus a shorter BCL2 (e.g., MCL1) isoform.

In alternative embodiments, nucleic acids used to practice the invention are made, isolated and/or manipulated by, e.g., cloning and expression of cDNA libraries, amplification of message or genomic DNA by PCR, and the like.

The nucleic acids used to practice this invention, whether RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including e.g. bacterial, fungal, mammalian, yeast, insect or plant cell expression systems.

Alternatively, nucleic acids used to practice this invention can be synthesized in vitro by well-known chemical synthesis techniques, as described in, e.g., Adams (1983) *J. Am. Chem. Soc.* 105:661; Belousov (1997) *Nucleic Acids Res.* 25:3440-3444; Frenkel (1995) *Free Radic. Biol. Med.* 19:373-380; Blommers (1994) Biochemistry 33:7886-7896; Narang (1979) *Meth. Enzymol.* 68:90; Brown (1979) Meth. Enzymol. 68:109; Beaucage (1981) *Tetra. Lett.* 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *MOLECULAR CLONING: A LABORATORY MANUAL* (2ND ED.), Vols. 1-3, Cold Spring Harbor Laboratory, (1989); *CURRENT PROTOCOLS IN MOLECULAR BIOLOGY*, Ausubel, ed. John Wiley & Sons, Inc., New York (1997); *LABORATORY TECHNIQUES IN BIOCHEMISTRY AND MOLECULAR BIOLOGY: HYBRIDIZATION WITH NUCLEIC ACID PROBES*, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

Nucleic acids or nucleic acid sequences used to practice this invention can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs). Compounds use to practice this invention include nucleic acids, i.e., oligonucleotides, containing known analogues of natural nucleotides. Compounds use to practice this invention include nucleic-acid-like structures with synthetic backbones, see e.g., Mata (1997) *Toxicol. Appl. Pharmacol.* 144:189-197; Strauss-Soukup (1997) *Biochemistry* 36:8692-8698; Samstag (1996) *Antisense Nucleic Acid Drug Dev* 6:153-156. Compounds use to practice this invention include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

Sequence information for designing primers for identifying isoforms of the BCL2 family in PCR reactions and/or for designing compounds, such as antisense, ribozymes, interfering RNA and the like to decrease the expression of BCL2 proteins in cancer stems cells is known in the art, for example, see U.S. Publication Nos. 2012/0172285 and 2009/0247613. Both of which are incorporated by reference herein.

In alternative aspects, compounds used to practice this invention include genes or any segment of DNA or RNA involved in producing a polypeptide chain; it can include regions preceding and following the coding region (leader and trailer) as well as, where applicable, intervening sequences (introns) between individual coding segments (exons). "Operably linked" can refer to a functional relationship between two or more nucleic acid (e.g., DNA or RNA) segments. In alternative aspects, it can refer to the functional relationship of transcriptional regulatory sequence to a transcribed sequence. For example, a promoter can be operably linked to a coding sequence, such as a nucleic acid used to practice this invention, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassettes" comprising a nucleotide sequence used to practice this invention, which can be capable of affecting expression of the nucleic acid, e.g., a structural gene or a transcript (e.g., encoding a DRP or antibody) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice this invention also include plasmids, expression vectors, recombinant viruses, any form of recombinant "naked DNA" vector, and the like. In alternative aspects, a "vector"

used to practice this invention can comprise a nucleic acid that can infect, transfect, transiently or permanently transduce a cell. In alternative aspects, a vector used to practice this invention can be a naked nucleic acid, or a nucleic acid complexed with protein or lipid. In alternative aspects, vectors used to practice this invention can comprise viral or bacterial nucleic acids and/or proteins, and/or membranes (e.g., a cell membrane, a viral lipid envelope, etc.). In alternative aspects, vectors used to practice this invention can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice this invention can be stably replicated by the cells during mitosis as an autonomous structure, or can be incorporated within the host's genome.

In alternative aspects, "promoters" used to practice this invention include all sequences capable of driving transcription of a coding sequence in a cell, e.g., a mammalian cell such as a brain cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

"Constitutive" promoters used to practice this invention can be those that drive expression continuously under most environmental conditions and states of development or cell differentiation. "Inducible" or "regulatable" promoters used to practice this invention can direct expression of the nucleic acid of the invention under the influence of environmental conditions or developmental conditions.

Kits and Instructions

The invention provides kits comprising compositions (e.g., MCL1, BCLX and BFl1 isoform detecting and/or isoform discriminating PCR primers) and/or instructions for practicing methods of the invention. As such, kits, cells, vectors and the like can also be provided.

EXAMPLES

Methods-BCL2

Patient Sample Preparation and FACS Sorting

Normal cord blood and adult peripheral blood samples were purchased from All Cells. CML samples were obtained from consenting patients at the University of California San Diego, Stanford University, the University of Toronto Health Network, MD Anderson and the University of Bologna according to Institutional Review Board approved protocols. CD34$^+$ cells were initially purified by magnetic bead separation (MACS; Miltenyi, Bergisch Gladbach, Germany) followed by FACS progenitor purification using human-specific CD34 and CD38 antibodies as previously described (Jaiswal, S., et al. *Proc Natl Acad Sci USA* 100, 10002-10007 (2003); Jamieson, C. H., et al. *N Engl J Med* 351, 657-667 (2004)). Peripheral blood mononuclear cells (PBMC) were extracted from peripheral blood following Ficoll density centrifugation, CD34$^+$ selected, stained with fluorescent conjugated antibodies, and analyzed and purified using a FACS Aria and Flowjo software as described (Jaiswal, S. et al. cited above and Jamieson, C. H., et al. cited above).

BCL2 Family Splice Isoform Analysis

Normal or CML CD34$^+$ cells were stained with mouse anti-human BCL2 (Dako) monoclonal antibody and analyzed by FACS. Quantitative RT-PCR to detect BCL2, MCL1, BCLX and BFL1 isoforms in FACS-sorted normal versus CML progenitors was performed with SYBR GreenER two-step qRT-PCR Kit (Invitrogen).

BCL2 genes were also analyzed in engrafted CML cells. Briefly, 20,000-50,000 CD34$^+$CD38$^+$lin$^-$ cells were FACS-sorted from engrafted tissues and analyzed using isoform-specific qRT-PCR or using an RT-PCR apoptosis-pathway OpenArray "nanoplate" (Invitrogen). BCL2 protein was also measured in engrafted tissue cells as described herein.

Quantitative RT-PCR 20,000-50,000 hematopoietic progenitor cells were sorted from the indicated cell populations using FACS, total RNA was isolated and cDNA was synthesized as described (see Jaiswal, S. et al. cited above and Jamieson, C. H., et al. cited above). Quantitative PCR (qRT-PCR) was performed in duplicate on an iCycler using SYBR GreenER Super Mix (Invitrogen, Carlsbad, Calif.), 5 ng of template mRNA, and 0.4 mM of each forward and reverse primer. Splice isoform-specific primers were designed for BCL2, MCL1, BCLX, and BFL1 and isoform specificity was confirmed by sequencing of each PCR product.

The following primers were used:

```
                                     (SEQ. ID. NO: 1)
BCL2L Forward:  atgtgtgtggagagcgtcaa (SEQ. ID. NO: 2)
BCL2L Reverse:  ttcagagacagccaggagaaa (SEQ. ID. NO: 3)
MCL1L Forward:  agaccttacgacgggttgg (SEQ. ID. NO: 4)
MCL1L Reverse:  aatcctgccccagtttgtta (SEQ. ID. NO: 5)
MCL1S Forward:  gaggaggacgagttgtaccg (SEQ. ID. NO: 6)
MCL1S Reverse:  actccacaaacccatccttg (SEQ. ID. NO: 7)
BCLXL Forward:  catggcagcagtaaagcaag (SEQ. ID. NO: 8)
BCLXL Reverse:  gaaggagaaaaaggccacaa (SEQ. ID. NO: 9)
BFL1L Forward:  gctgggaaaatggctttg (SEQ. ID. NO: 10)
BFL1L Reverse:  tcagaaaaattaggccggttt (SEQ. ID. NO: 11)
BCR-ABL Forward:  ctccagactgtccacagcat (SEQ. ID. NO: 12)
BCR-ABL Reverse:  ccctgaggctcaaagtcaga (SEQ. ID. NO: 13)
HPRT Forward:  cgtcttgctcgagatgtgatg
```

HPRT Reverse: tttatagccccccttgagcac (SEQ. ID. NO: 14)

mRNA levels for each transcript were normalized to HPRT and compared using the delta-delta CT method.

BCL2 FACS Analyses

Normal, CP CML and BC CML CD34+ selected cells were stained with lineage antibodies and progenitor antibodies as described previously (see Jaiswal, S. et al. cited above and Jamieson, C. H., et al. cited above), and fixed with 0.8% paraformaldehyde (PFA) for 10 min Cells were then washed and stained overnight with a FITC-conjugated mouse monoclonal antibody specific for human BCL2 (Dako, #F7053) or isotype-control antibody diluted in 0.15% Saponin (TCI America). The next day the cells were washed and analyzed using a FACS Aria and Flowjo software. Mean fluorescence intensity (MFI) for BCL2 was measured for each CML sample and normalized to a normal control sample in the same experiment.

Transplantation, In Vivo Dasatinib and Sabutoclax Treatment, Engraftment Analysis and Serial Transplantation Immunocompromised RAG2$^{-/-}$y$_c^{-/-}$ mice were bred and maintained in the University of California San Diego Moores Cancer Center vivarium. Neonatal mice were transplanted intrahepatically with 50,000-200,000 CD34+ cells according to our previously published methods (see Jaiswal, S. et al. cited above and Jamieson, C. H., et al. cited above). Transplanted mice were screened for tumor formation or human engraftment in peripheral blood by FACS at 6-8 weeks post-transplant. Upon detection of tumors, peripheral blood engraftment, or at 8-12 weeks post-transplant engrafted mice were treated for 2 weeks with dasatinib (daily, 50 mg/kg/day in 50% PEG, 50% PBS by oral gavage), sabutoclax (3 days per week, 5 mg/kg/day in 10% EtOH, 10% Cremaphor EL (Sigma Aldrich) 80% PBS by IP injection), or drug vehicles. Twenty-four hours post-treatment (10-14 weeks post-transplant), mice were euthanized and single cell suspensions of hematopoietic tissues were analyzed for human engraftment by FACS as described previously (see Jaiswal, S. et al. and Jamieson, C. H., et al. cited above). For in vivo combination studies, dasatinib was used at 25 or 50 mg/kg while sabutclax was used at 1.25 or 2.5 mg/kg with the same dosing regimen described above. For serial transplantation, a mix of whole mouse bone marrows was made from mice in the same treatment group. Total bone marrow cells were then counted by using Guava ViaCount Reagent and analysis on a Guava PCA system (Millipore), and transplanted in equal numbers into secondary neonatal recipients by intrahepatic injection. 250,000 whole bone marrow cells per mouse were injected.

DiR Staining and Measurement by FACS 50,000 CD34+ CML cells were isolated as described previously and stained with 4 mg/mL DiR (Invitrogen) in PBS according to the manufacturer's specifications. DiR stained cells were then washed and transplanted into neonatal mice. After 18 weeks, mice were sacrificed and hematopoietic tissues were analyzed by FACS for human DiR+ cells. DiR MFI was measured in human CD38+lin−PI− cells engrafted in each tissue.

FACS Cell Cycle Analysis

Single cell suspensions of bone marrow cells from mice treated with sabutoclax or vehicle were immunostained with Alexa405-conjugated anti-human CD45 (Invitrogen), Alexa647-anti-human CD38 (Ab Serotec) and biotin-anti-human CD34 (Invitrogen) plus Alexa488-strepavidin (Invitrogen) in 2% fetal bovine serum/PBS-followed by live cell staining using the LIVE/DEAD® Fixable Near-IR Dead Cell Stain Kit (Invitrogen). Surface stained cells were then fixed in 70% ethanol overnight. Fixed, surface stained cells were immunostained with PE-conjugated anti-Ki-67 (BD) in 0.15% saponin/2% fetal bovine serum/PBS-, washed twice in saponin-containing staining media and incubated with 7-AAD (Invitrogen, 10 μg/mL in 0.1M sodium citrate/5 mM EDTA pH8.0/0.15M NaCl/0.5% BSA/0.02% saponin). Stained samples were analyzed using a FACSAria and FlowJo.

Bone marrow IHC and IF

For IHC, femurs were harvested from transplanted, treated animals, fixed and decalcified in Cal-Ex II (Fisher Scientific, Fair Lawn, N.J.) for 48 hrs, followed by standard tissue processing, paraffin-embedding and sectioning. Paraffin tissue sections were deparaffinized, rehydrated, and boiled in antigen retrieval solution (BD, California) (pH 6.0) for 10 min to retrieve antigen. Tissues were blocked with 5% bovine serum albumin (BSA) and 0.25% Triton X-100 in PBS for 30 min and incubated with primary antibody in PBS with 1% BSA at 4° C. for 16 h. Primary antibodies used were human CD45 (Abcam) and ki67 (BD). IHC staining was then carried out with LSAB System-HRP Kit (Dako Cytomation, Hamburg, Germany) according to manufacturer's protocol using methyl green (Sigma Aldrich) as counterstaining. Omission of primary antibodies was used as a negative control and showed no staining. All sections were mounted before examination using a Nikon Eclipse E600 microscope.

For IF, femurs were fixed in 4% PFA (EMS, Hatfield, Pa.) for 1 hour, decalcified in 0.23M EDTA pH 7.0 for 4 days by changing the decalcifying solution twice daily, dehydrated in 30% sucrose and frozen in OCT. For immunostaining, cryoprotected tissue was sectioned at 10 mm, wash with PBS-, fixed with 4% PFA for 10 minutes and rinsed with PBS-. Sections were incubated with 5% normal donkey serum/0.2% Triton X-100 for 1 hour at room temperature followed by incubation with primary antibodies overnight at 4° C. Mouse antibodies were used with MOM kit (Vector, Burlingame, Calif.). Mouse antibodies were used with MOM kit (Vector, Burlingame, Calif.). Primary antibodies used were anti-phospho-histone H3, Ser10 (1:500, Cell Signaling, Inc.), anti-human Ki-67 (1:300, Spring Bioscience), anti-human CD34 (1:250, BD Biosciences), Alexa 647-conjugated anti-human CD38 (1:25, Serotec) and FITC-conjugated antihuman BCL2 (1:25, Dako). Slides were washed in PBS- and incubated with secondary antibody (Alexa 594-conjugated donkey anti-mouse or rabbit, Invitrogen) for 1 hour at room temperature. Stained sections were mounted using Prolong® Gold antifade with DAPI (Invitrogen). Epifluorescent images were acquired using confocal microscopy (Zeiss LSM510 or Olympus Fluoview FV10i) and Adobe Photoshop CS5.

For apoptosis analysis, bone marrows are stained using the ApopTag fluorescein in situ TUNEL apoptosis detection kit (Chemicon, #S7110) following the manufacturer's protocol. Sections are mounted as above. Images are acquired using an Applied Imaging Ariol SL-50 automated scanning microscope and image analysis system.

RT-PCR Apoptosis Array

FACS-sorted progenitors cells are analyzed using OpenArray "nanoplate" technology (Invitrogen). Briefly, 20,000 progenitor cells str sorted from the bone marrow and spleen of BC engrafted mice into lysis buffer (Cell-to-Ct kit, Life Technologies) followed by DNAse treatment and reverse transcription reaction. 20 ul of cDNA is pre-amplified for 12 cycles with a pool of gene-specific Taqman assays spotted on Taqman Apoptosis OpenArray. The diluted (1:20) pre-amplified cDNA (1.5 ul) is mixed with GeneFast Taqman PCR mix (3.5 ul) (Life Technologies, Inc) and dispensed into the OpenArray plate. Twenty-four cDNA samples are tested simultaneously per OpenArray plate. Real-time PCR occurs in a computer-controlled imaging NT OpenArray thermal cycler. The amplification curves for each throughhole in the array are constructed from collected images, from which cycle threshold (CT) is computed and used for further data analysis. Gene levels are normalized to the geometric mean of RPLPO, ACTB, PPIA, PGK1 and B2M and are compared using the delta-delta CT method.

Bone Marrow BCL2 and MCL1 IHC Analysis

Bone specimens were fixed and mildly decalcified in Bouin's solution (Sigma-Aldrich, St. Louis, Mo.) for 8 h at room temperature, then postfixed in zinc-containing buffered formalin (Z-Fix; Anatech Ltd., Battle Creek, Mich.) for 3 days at 4° C., and embedded in paraffin. Dewaxed tissue sections (4-5 μm) were immunostained using mouse monoclonal antibody to CD34 (DakoCytomation, Carpinteria, Calif.) and rabbit polyclonal BCL2 and MCL1 antibodies against synthetic peptides. The slides were scanned at an absolute magnification of 400× (resolution of 0.25 μm/pixel (100,000 pix/in.)) using the Aperio ScanScope CS system (Aperio Technologies, Vista, Calif.). The Spectrum Analysis algorithm package and ImageScope analysis software (version 9; Aperio Technologies, Inc.) were applied to quantify IHC stainings.

SL/M2 Co-Culture

The mouse bone marrow stromal cell lines M2-10B4 (M2) and SL/SL (SL) are provided by StemCell Technologies and are passaged according to previously published methods (Hogge, D. E., et al., *Blood* 88, 3765-3773 (1996)). One day prior to co-culture, the cell lines are treated with mitomycin-C (1 mg/ml for 3 hours) and plated in a 1:1 mixture in total concentration of 100,000/ml. After 24 hours, 10,000-20,000 CD34$^+$ CML or normal cells are plated on top of the adherent SL/M2 cells, cultured for 1-4 weeks in Myelocult H5100 media (StemCell Technologies) and frequency of live human progenitor cells are quantified by FACS.

In Vitro Drug Treatment and Apoptosis Analysis

Cultures of CD34$^+$ CML and normal cells were maintained alone in Stempro media (Invitrogen) or on SL/M2 stroma as described above. One day after plating, cultured cells were treated with different concentrations of sabutoclax diluted in DMSO. After 1 week of culture, live CD45$^+$ CD34$^+$CD38$^+$lin$^-$ cells were quantified by FACS analysis. For analysis of apoptosis, treated cells were harvested after 24 hours and analyzed for activated caspase-3 by FACS using the NucView-488 assay (Biotium, Hayward, Calif.) according to the manufacturer's specifications. Best-fit lines and IC$_{50}$ determinations were generated by fitting the experimental data using a sigmoidal dose-response nonlinear regression model with vehicle controls set at 1 nM to facilitate plotting the data on a log-scale.

Colony Assays

Following in vitro culture in Stempro media or with SL/M2 stroma, human cells were harvested, counted by trypan blue exclusion or by using Guava ViaCount Reagent and analysis on a Guava PCA system (Millipore), and 100-200 cells were plated per well of a 24-well plate in Methocult media (Stemcell Technologies). After 2 weeks, total colonies were counted.

Ex Vivo Combination Experiment

Neonatal mice were transplanted with 10,000 CD34$^+$ BC cells and were treated with 5 mg/kg sabutoclax (n=3) or vehicle (n=3) starting at 8 weeks post-transplant as previously described. After 72 hours of treatment the mice were sacrificed, bone marrow was harvested, and progenitors were FACS-sorted from each individual mouse. 10,000-20,000 sorted progenitors from the individual mice were then distributed per well onto confluent SL/M2 stroma in 24-well plates and treated with increasing doses of dasatinib for 1 week. After the 1-week treatment the co-cultures were harvested and analyzed for live BC progenitor cells by FACS as described above.

Results

Although studies have linked BCL2 upregulation with chronic phase (CP) progression to blast phase (BC) in chronic myelooid leukemia (CML), most have focused on BCR-ABL-expressing cell lines (Sanchez-Garcia, I. & Grutz, G. *Proc Natl Acad Sci USA* 92, 5287-5291 (1995); Amarante-Mendes, G. P., et al. *Oncogene* 16, 1383-1390 (1998); Gesbert, F. & Griffin, J. D. *Blood* 96, 2269-2276 (2000)); or bulk CD34$^+$ cells (Horita, M., et al. *J Exp Med* 191, 977-984 (2000). Aichberger, K. J., et al. *Blood* 105, 3303-3311 (2005). Radich, J. P., et al. *Proc Natl Acad Sci USA* 103, 2794-2799 (2006)) rather than functionally validated BC leukemia stem cells (LSC). Recent reports show that BCL2 family genes encode splice variants with alternate functions. (Moore, M. J., et al., *Cell* 142, 625-636 (2010)). However, there is relatively little information on BCL2 splice variant expression in human BC LSC. As disclosed herein splice-isoform specific qRT-PCR was used to analyze BCL2 family isoform expression in sorted primary normal, CP and BC progenitors. BC LSC expressed significantly higher levels of pro-survival BCL2L, MCL1 L, BCLXL and BFL1L than CP progenitors (FIG. 2). Both qRT-PCR and RNA sequencing also revealed significant overrepresentation of MCL1 long isoforms compared with short isoforms in BC LSC (FIG. 6). These data demonstrate that pro-survival BCL2 family genes are globally upregulated in CML LSC with disease progression.

Quiescent BC LSC Engraft in the Marrow Niche and are Resistant to Dasatinib

In addition to altered BCL2 isoform expression, both in vitro and in vivo studies suggest that supportive microenvironments render LSC quiescent and resistant to therapy (Barnes, D. J. & Melo, J. V. *Cell Cycle* 5, 2862-2866 (2006); Holyoake, T., Jiang, X., Eaves, C. & Eaves, *Blood* 94, 2056-2064 (1999); Saito, Y., et al. *Nat Biotechnol* 28, 275-280 (2010); Bewry, N. N., et al. *Mol Cancer Ther* 7, 3169-3175 (2008)). To investigate how the microenvironment contributes to LSC survival we examined BC LSC in various hematopoietic niches using a xenograft model. Following human BC CML CD34$^+$ cell transplantation into neonatal RAG2$^{-/-}\gamma_c^{-/-}$ mice (Abrahamsson, A E, et al., cited above) myeloid sarcoma formation and leukemic engraftment was detectable in hematopoietic tissues at 8-10 weeks post-transplant (data not shown). To quantitatively assess whether quiescent BC LSC had a predilection for a particular microenvironment, leukemic progenitors were labeled with DiR, a membrane-bound fluorescent dye that persists only in non-dividing cells, and DiR fluorescence was measured in leukemic cells in the various environments. Marrow-resident BC cells retained significantly more DiR fluorescence than those engrafted in other tissues (FIG. 4a). We next examined the cell-cycle profile of marrow-engrafted cells using Ki67/7-AAD flow-cytometric analysis, which demonstrated a distinct population of G0 (Ki67low7-AADlow) progenitors (FIG. 4b-c). This observation was confirmed by immunohistochemical and immunofluorescence analysis of BC-engrafted bone marrow using Ki67 and the mitosis marker phospho-Histone-H3 (pHis-H3) (FIG. 4d-e). Results also revealed enrichment of pHis-H3- and Ki-67low CD45+CD34+CD38+ leukemic cells adjacent to the endosteum (FIG. 4d-e), similar to that reported in AML LSC xenograft models 31. Together these data indicate that quiescent BC LSC reside in the marrow niche and may preferentially reside in the endosteal space.

We next examined the efficacy of dasatinib, a BCR-ABL targeted tyrosine kinase inhibitor (TKI), against LSC in the various hematopoietic niches. Mice transplanted with BC CD34+ cells had high engraftment of human CD45+ cells in all hematopoietic tissues. CD34+CD38+lin− cells were also detectable in all tissues. Dasatinib treatment (50 mg/kg) significantly reduced CD45+ leukemic burden in all tissues compared to vehicle treated controls (FIG. 3a). However, a dasatinib-resistant population remained in the marrow after treatment and was even more evident when engraftment of CD34+CD38+lin− cells was examined Importantly, TKI-resistance was not due to a lack of drug availability in the marrow because FACS-sorted marrow-CD34+CD38+lin− cells had significant reduction in CRKL phosphorylation, a direct measure of BCR-ABL activity, following dasatinib treatment (data not shown). Also, the cell cycle profile of marrow-engrafted LSC after dasatinib treatment indicated a significant shift towards quiescence (FIG. 1(d)). Together, these data demonstrate that quiescent BC LSC in the bone marrow microenvironment are protected from TKI treatment through BCR-ABL-independent mechanisms. Moreover, quiescent BC LSC are enriched in the marrow following TKI-treatment.

Sabutoclax Sensitizes Marrow-Niche Engrafted BC LSC to Dasatinib

To examine the necessity of pro-survival BCL2 family expression for LSC function, we tested the efficacy of sabutoclax against LSC in vivo (FIG. 5). In BC-transplanted mice, sabutoclax (5 mg/kg) significantly reduced LSC engraftment in all hematopoietic tissues including bone marrow (FIG. 5b). BC LSC—engrafted marrow had a reduced amount of BCL2 and MCL1 immunopositive cells following sabutoclax treatment (data not shown) as well as a slight increase in G2/S cells (FIG. 7) and increased TUNEL+apoptotic cells suggesting that quiescent BC cells were killed by apoptosis.

We next examined whether sabutoclax could sensitize marrow niche LSC to TKIs. BC-engrafted mice were treated with sabutoclax (1.25 mg/kg), dasatinib (25 mg/kg) or a combination of the two drugs and LSC engraftment was analyzed by FACS. Lower doses of both drugs were used so that any combined effect could be more easily resolved. While dasatinib and sabutoclax alone had no significant effect on marrow LSC engraftment at these lower doses, there was significant reduction in marrow LSC after combination treatment compared to vehicle treated controls (Table 1). At higher doses (50 mg/kg dasatinib, 2.5 mg/kg sabutoclax), this difference was more pronounced and there was ~90% reduction in LSC burden following combination treatment (Table 1).

Figure 8:
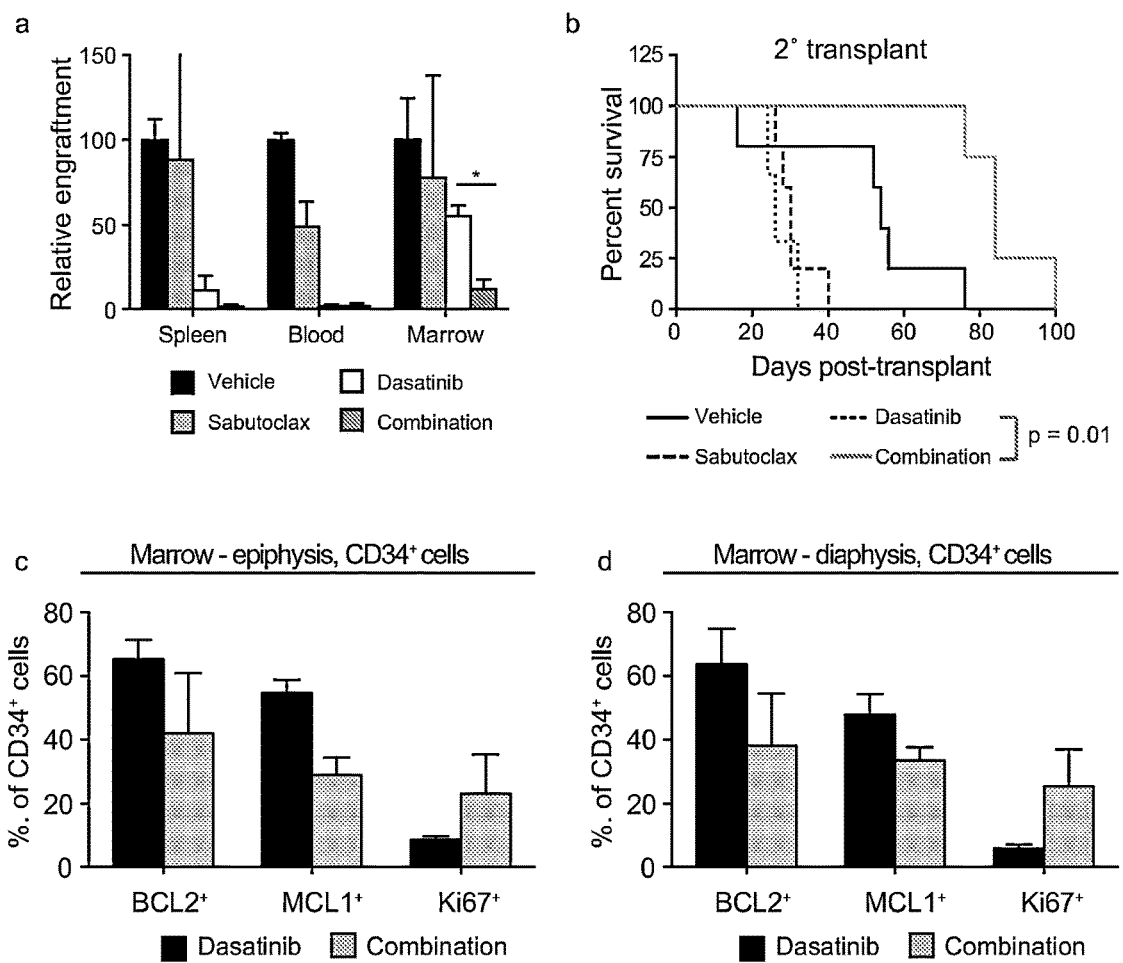
FIG. 8 Sabutoclax sensitizes BC LSC to dasatinib treatment in vivo. (a) Relative engraftment of BC progenitors in marrow following treatment with vehicle (n=2), sabutoclax (2.5 mg, n=2), dasatinib (50 mg/kg, n=3) and sabutoclax in combination with dasatinib (n=2). Statistical analysis is by unpaired t-test. b) Survival of mice following serially transplant with vehicle—(n=5), sabutoclax—(n=5), dasatinib—(n=3) and combination-treated (n=4) marrow. Statistical analysis is by log-rank test. c) Quantification of BCL2, MCL1 and Ki67 staining in epiphyseal- and diaphyseal-engrafted (d) CD34$^+$ cells following treatment with dasatinib (n=3) versus dasatinib in combination with sabutoclax (n=3). All bar graphs in FIG. 8 show mean+/−SEM.

We also examined combination treated marrow in more detail by immunohistochemical analysis. Compared to dasatinib treatment alone, combination-treated marrows had a trend toward reduction of BCL2 and MCL1 protein as well as a trend toward increased Ki67 expression (FIG. 8c-d). These results suggest that sabutoclax sensitizes quiescent, BCL2 family-expressing cells to dasatinib-mediated cell death. Finally, to test whether functional LSC had truly been eliminated, we serially transplanted treated bone marrow into secondary recipients and monitored survival time. Mice that received combination-treated marrow had a significant survival advantage compared to those that received dasatinib-treated marrow at both doses tested (FIG. 8(b)). Overall our data demonstrate that dasatinib alone, while effective at reducing primary leukemic burden, does not significantly eradicate bone marrow-resident LSC. In contrast, combined dasatinib and sabutoclax therapy significantly inhibits both primary and serial LSC engraftment suggesting that TKI-resistance has been abrogated.

TABLE 1

Effects of sabutoclax in combination with dastinib on BC LSC engraftment in vivo

| | Mean (SEM) engraftment of CD34+CD38+ cells | | | 2° TP - Median survival (days) |
|---|---|---|---|---|
| | Spleen | Blood | Marrow | |
| Low Dose Treatment | | | | |
| Vehicle (n = 10) | 16.8 (3.7) | 12.5 (4.8) | 35.4 (12.4) | 78.5 (n = 12) |
| Sabutoclax (n = 9) | 12 (2.7) | 11.0 (3.8) | 34.2 (12.5) | 74 (n = 10) |
| Dasatinib (n = 9) | 2.0 (0.8) | 2.1 (0.9) | 28.8 (10.7) | 79 (n = 10) |
| Combination (n = 11) | 0.6 (0.3) | 0.6 (0.3) | 15.5 (6.0) | 88 (n = 13) |
| p value (dasatinib vs. combination) | 0.07 | 0.07 | 0.22 | 0.054 |
| High Dose Treatment | | | | |
| Vehicle (n = 2) | 10.3 (0.4) | 27.7 (3.4) | 38.58 (9.6) | 57 (n = 5) |
| Sabutoclax (n = 2) | 5.1 (1.5) | 24.5 (17.6) | 30.01 (23.2) | 45 (n = 5) |
| Dasatinib (n = 3) | 0.2 (0.07) | 3.1 (2.4) | 21.23 (2.4) | 43 (n = 3) |
| Combination (n = 2) | 0.19 (0.16) | 0.4 (0.37) | 4.54 (2.3) | 72 (n = 4) |
| p value (dasatinib vs. combination) | 0.91 | 0.44 | 0.018 | 0.01 |

A number of embodiments of the invention have been described. Nevertheless, it will be understood that various modifications may be made without departing from the spirit and scope of the invention. Accordingly, other embodiments are within the scope of the following claims.

What is claimed is:

1. A method for sensitizing a quiescent leukemia stem cell to a BCR-ABL inhibitor in a subject in need thereof, comprising: administering to the cell a composition comprising sabutoclax in an amount sufficient to sensitize the leukemia stem cell to the BCR-ABL inhibitor, wherein the BCR-ABL inhibitor comprises dasatinib.

2. The method of claim 1, wherein the BCR-ABL inhibitor further comprises imatinib, bafetinib, bosutinib, nilotinib, or AP24534.

3. The method of claim 1, wherein the subject has chronic myeloid leukemia.

4. A method of treating chronic myeloid leukemia comprising: administering to a subject in need thereof a composition comprising sabutoclax and at least one tyrosine kinase inhibitor.

5. The method of claim 4, wherein the tyrosine kinase inhibitor comprises dasatinib, imatinib, bafetinib, bosutinib, nilotinib, or AP24534.

6. The method of claim 4, wherein the chronic myeloid leukemia is in the blast crisis phase.

7. The method of claim 4, wherein the at least one tyrosine kinase inhibitor comprises dasatinib.

* * * * *